United States Patent
Ladel et al.

(10) Patent No.: US 12,383,603 B2
(45) Date of Patent: Aug. 12, 2025

(54) MARKERS USEFUL IN ENRICHMENT STRATEGIES FOR THE TREATMENT OF OSTEOARTHRITIS

(71) Applicant: MERCK PATENT GMBH, Darmstadt (DE)

(72) Inventors: Christoph H. Ladel, Darmstadt (DE); Hans Guehring, Geisenheim (DE); Anne-Christine Bay-Jensen, Copenhagen (DK); Morten Karsdal, Copenhagen (DK); Per Qvist, Copenhagen (DK)

(73) Assignee: Merck Patent GmbH, Darmstadt (DE)

( * ) Notice: Subject to any disclaimer, the term of this patent is extended or adjusted under 35 U.S.C. 154(b) by 363 days.

(21) Appl. No.: 17/274,457

(22) PCT Filed: Sep. 9, 2019

(86) PCT No.: PCT/EP2019/074003
§ 371 (c)(1),
(2) Date: Mar. 9, 2021

(87) PCT Pub. No.: WO2020/053155
PCT Pub. Date: Mar. 19, 2020

(65) Prior Publication Data
US 2022/0047674 A1    Feb. 17, 2022

(30) Foreign Application Priority Data

Sep. 10, 2018    (EP) .................................... 18193351

(51) Int. Cl.
| | | |
|---|---|---|
| *A61K 38/18* | (2006.01) |
| *A61K 38/23* | (2006.01) |
| *A61P 19/02* | (2006.01) |
| *G01N 33/68* | (2006.01) |

(52) U.S. Cl.
CPC ...... *A61K 38/1825* (2013.01); *A61K 38/1841* (2013.01); *A61K 38/1875* (2013.01); *A61K 38/23* (2013.01); *A61P 19/02* (2018.01); *G01N 33/6887* (2013.01); *G01N 2333/78* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 8,207,115 B2 | 6/2012 | Gimona et al. |
| 9,326,944 B2 | 5/2016 | Cerreti et al. |
| 9,724,388 B2 | 8/2017 | Ladel et al. |
| 9,795,714 B2 | 10/2017 | Canal et al. |
| 9,889,179 B2 | 2/2018 | Ladel et al. |
| 10,086,112 B2 | 10/2018 | Ladel et al. |
| 10,221,456 B2 | 3/2019 | Ladel et al. |
| 10,293,051 B2 | 5/2019 | Lo Presti et al. |
| 11,467,169 B2 | 10/2022 | Ladel et al. |
| 11,513,128 B2 * | 11/2022 | Ladel .................... A61P 19/04 |
| 2007/0207480 A1 | 9/2007 | Gobezie |
| 2007/0292892 A1 | 12/2007 | Sandell et al. |
| 2009/0299769 A1 | 12/2009 | Dam et al. |
| 2010/0016223 A1 | 1/2010 | Gimona et al. |
| 2010/0098775 A1 | 4/2010 | Bukowski et al. |
| 2012/0115137 A1 | 5/2012 | Kornman et al. |
| 2015/0203592 A1 | 7/2015 | Wang |
| 2015/0218637 A1 | 8/2015 | Ladel et al. |
| 2017/0299611 A1 | 10/2017 | Ruff |
| 2019/0161801 A1 | 5/2019 | Ladel et al. |
| 2021/0231680 A1 | 7/2021 | Ladel et al. |
| 2021/0231681 A1 | 7/2021 | Ladel et al. |
| 2023/0251271 A1 | 8/2023 | Ladel et al. |
| 2023/0258659 A1 | 8/2023 | Ladel et al. |

FOREIGN PATENT DOCUMENTS

| | | |
|---|---|---|
| CN | 104736723 A | 6/2015 |
| CN | 108472290 A | 8/2018 |
| JP | 2009-257842 A | 11/2009 |
| WO | WO-1998/016644 A1 | 4/1998 |
| WO | WO-2004/032849 A2 | 4/2004 |
| WO | WO-2006/063362 A1 | 6/2006 |
| WO | WO-2008/023063 A2 | 2/2008 |
| WO | WO-2009/135218 A2 | 11/2009 |
| WO | WO-2012/172072 A1 | 12/2012 |
| WO | WO-2014/023703 A1 | 2/2014 |

(Continued)

OTHER PUBLICATIONS

Sugiyama et al. (2003, Ann Rheum Dis 62:27-32).*
Takahashi et al. (1999, Osteoarthritis and Cartilage 7:182-190).*
Alaoui-Ismaili, M.H. and Falb, D., Design of second generation therapeutic recombinant bone morphogenetic proteins, Cytokine Growth Factor Rev., 20(5-6):501-507 (2009).
Bay-Jensen, A.C. et al. Osteoarthritis Year in Review 2015: Soluble Biomarkers and the BIPED Criteria, Osteoarthritis Cartilage, 24(1):9-20 (2016).
Beers, M.H. et al., The Merck Manual of Diagnosis and Therapy, Merck, 17th edition, 7 pages, (1999).

(Continued)

*Primary Examiner* — Elizabeth C. Kemmerer
(74) *Attorney, Agent, or Firm* — Choate, Hall & Stewart LLP; Michael A. Shinall; Stephany Foster

(57) ABSTRACT

The present invention relates to pharmacogenetics, more specifically to strategies involving biomarkers associated with the clinical response to a compound before or during treatment of a cartilage disorder, such as osteoarthritis. The present invention more particularly relates to the combination of JSW measurements and level of specific proteins present in the blood, serum, synovial fluid or in the urine, which can be used in strategies such as patients' enrichment in clinical trials, patients' selection strategy before or during treatment or for adapting the treatment of a patient in the frame of treatments for cartilage disorder, such as osteoarthritis.

15 Claims, 7 Drawing Sheets
Specification includes a Sequence Listing.

(56) References Cited

FOREIGN PATENT DOCUMENTS

| WO | WO-2014/023704 A1 | 2/2014 |
|---|---|---|
| WO | WO-2015/097233 A1 | 7/2015 |
| WO | WO-2015/097236 A2 | 7/2015 |
| WO | WO-2015/124731 A1 | 8/2015 |
| WO | WO-2015/124735 A1 | 8/2015 |
| WO | WO-2015/124739 A1 | 8/2015 |
| WO | WO-2016/120387 A1 | 8/2016 |
| WO | WO-2017/079765 A1 | 5/2017 |
| WO | WO-2019/063756 A1 | 4/2019 |
| WO | WO-2019/063758 A1 | 4/2019 |
| WO | WO-2020/053155 A1 | 3/2020 |

OTHER PUBLICATIONS

Bellamy, N. et al. Validation Study of WOMAC: A Health Status Instrument for Measuring Clinically Important Patient Relevant Outcomes to Antirheumatic Drug Therapy in Patients with Osteoarthritis of the Hip or Knee. J. Rheumatol., 15(12):1933-1840 (1988).

Bhattacharya, R. et al., Impact of genetic variation on three dimensional structure and function of proteins, PLoS One, 12(3):e0171355 (2017).

Brittberg, M. et al. ICRS Cartilage Injury Evaluation Package, ICRS 2000 Standards Workshop, 16 Pages, (2000).

Clinical Trial Protocol, Sprifermin Phase II Trial of Sprifermin in Knee OA EMR700692_006, Merck KGaA, Mar. 5, 2013, <https://clinicaltrials.gov/ProvidedDocs/64/NCT01919164/Prot_000.pdf>.

Duclos, M.E. et al., Significance of the serum CTX-II level in an osteoarthritis animal model: a 5-month longitudinal study, Osteoarthritis Cartilage, 18(11):1467-1476 (2010).

Ellsworth, J. L. et al. Fibroblast Growth Factor-18 is a Trophic Factor for Mature Chondrocytes and Their Progenitors, Osteoarthritis Cartilage, 10(4):308-320 (2002).

Fenton, A.W. et al., Rheostat positions: A new classification of protein positions relevant to pharmacogenomics, Med. Chem. Res., 29(7):1133-1146 (2020).

Gigout, A. et al. Sprifermin (rhFGF18) Enables Proliferation of Chondrocytes Producing a Hyaline Cartilage Matrix, Osteoarthritis Cartilage, 25(11):1858-1867 (2017).

Grad, S. et al., Systemic blood plasma CCL5 and CXCL6: Potential biomarkers for human lumbar disc degeneration, Eur. Cell. Mater., 31:1-10 (2016).

Gudmann, N.S. et al., Cartilage Turnover Reflected by Metabolic Processing of Type II Collagen: A Novel Marker of Anabolic Function in Chondrocytes, Int. J. Mol. Sci., 15(10):18789-18803 (2014).

Gudmann, N.S. et al., Chondrocyte activity is increased in psoriatic arthritis and axial spondyloarthritis, Arthritis Res. Ther., 18(1):141 (2016).

Guo, H.H. et al., Protein tolerance to random amino acid change, PNAS USA, 101(25):9205-9210 (2004).

Haque, T. et al., A Review of FGF18: Its Expression, Signaling Pathways and Possible Functions During Embryogenesis and Post-Natal Development, Histol Histopathol, 22(1):97-105 (2007).

Hosnijeh, F.S. et al., Association Between Biomarkers of Tissue Inflammation and Progression of Osteoarthritis: Evidence from the Rotterdam Study Cohort, Arthritis Res. Ther., 18:81 (2016).

Karsdal, M.A. et al. Disease-Modifying Treatments for Osteoarthritis (DMOADs) of the Knee and Hip: Lessons Learned from Failures and Opportunities for the Future, Osteoarthritis Cartilage, 24(12):2013-2021 (2016).

Krishnan, Y. and Grodzinsky, A.J. et al., Cartilage diseases, Matrix Biol., 71-72:51-69 (2018).

Lotz, M.K., Posttraumatic Osteoarthritis: Pathogenesis and Pharmacological Treatment Options, Arthritis Res. Ther., 12(3):211 (2010).

Maijer, K.I. et al., Neo-Epitopes-Fragments of Cartilage and Connective Tissue Degradation in Early Rheumatoid Arthritis and Unclassed Arthritis, PLoS One, 11(3):e0149329 (2016).

Munk, H.L. et al., Cartilage collagen type II seromarker patterns in axial spondyloarthritis and psoriatic arthritis: associations with disease activity, smoking and HLA-B27, Rheumatol. Int., 36(4):541-549 (2016).

Rowshan, H.H. et al., Pseudomonas aeruginosa infection of the auricular cartilage caused by "high ear piercing": a case report and review of the literature, J. Oral. Maxillofac. Surg., 66(3):543-546 (2008).

Sherwood, J. et al., A homeostatic function of CXCR2 signalling in articular cartilage, Ann. Rheum. Dis., 74(12):2207-2215 (2015).

Shimoaka, T. et al. Regulation of Osteoblast, Chondrocyte, and Osteoclast Functions by Fibroblast Growth Factor (FGF)-18 in Comparison with FGF-2 and FGF-10, J. Biol. Chem., 277(9):7493-500 (2002).

Siebuhr, A.S. et al., CRP and a Biomarker of Type I Collagen Degradation, C1M Can Differentiate Anti-Inflammatory Treatment Response in Ankylosing Spondylitis, Biomark. Med., 10(2):197-208 (2016).

Siebuhr, A.S. et al., Identification and Characterisation of Osteoarthritis Patients with Inflammation Derived Tissue Turnover, Osteoarthritis Cartilage, 22(1):44-50 (2014).

Siebuhr, A.S. et al., Serological Identification of Fast Progressors of Structural Damage with Rheumatoid Arthritis, Arthritis Res. Ther., 15(4):R86 (2013).

Tokuriki, N and Tawfik, D.S., Stability effects of mutations and protein evolvability, Curr. Opin. Struc. Biol., 19(5):596-604 (2009).

Valdes, A.M. et al., Intercritical Circulating Levels of Neo-Epitopes Reflecting Matrixmetalloprotease-Driven Degradation as Markers of Gout and Frequent Gout Attacks, Rheumatology (Oxford), 55(9):1642-1646 (2016).

Wolfe, F., Determinants of WOMAC Function, Pain and Stiffness Scores: Evidence for the Role of Low Back Pain, Symptom Counts, Fatigue and Depression in Osteoarthritis, Rheumatoid Arthritis and Fibromyalgia, Rheumatology (Oxford), 38(4):355-361 (1999).

Written Opinion for PCT/EP2018/076395, filed Sep. 28, 2018, 10 pages, (mailed Nov. 6, 2018).

Bagger, Y. Z. et al. "Oral salmon calcitonin induced suppression of urinary collagen type II degradation in postmenopausal women: A new potential treatment of osteoarthritis" Bone, 2005, pp. 425-430, vol. 37, No. 3.

Buckland-Wright, J. C. et al. "Quantitative Microfocal Radiography Detects Changes in OA Knee Joint Space Width in Patients in Placebo Controlled Trial of NSAID Therapy" The Journal of Rheumatology, 1995, pp. 937-943, vol. 22, No. 5.

Christgau, S. et al. "Osteoarthritic patients with high cartilage turnover show increased responsiveness to the cartilage protecting effects of glucosamine sulphate" Clinical and Experimental Rheumatology, 2004, pp. 36-42, vol. 22.

Jubb, R. W. et al. "A One-Year, Randomised, Placebo (Saline) Controlled Clinical Trial of 500-730 KDA Sodium Hyaluronate (Hyalgan®) on the Radiological Change in Osteoarthritis of the Knee" International Journal of Clinical Practice, 2003, pp. 467-474, vol. 57, No. 6.

Mazzuca, S. A. et al. "Is conventional radiography suitable for evaluation of a disease-modifying drug in patients with knee osteoarthritis?" Osteoarthritis and Cartilage, 1997, pp. 217-226, vol. 5, No. 4.

Sawitzke, A. D. et al. "The Effect of Glucosamine and/or Chondroitin Sulfate on the Progression of Knee Osteoarthritis: A GAIT Report" Arthritis Rheum. Oct. 2008, pp. 1-16, vol. 58, No. 10.

Written Opinion in International Application No. PCT/EP2019/074003, Oct. 11, 2019, pp. 1-12.

Attur, M. et al., 391 Association of Interleukin-1 receptor antagonist (IL-IRN) TTC Haplotype with radiographic knee OA severity in meta-analysis, Osteo. Cart., 18:S172 (2010).

Attur, M. et al., 392 Interleukin-1 receptor antagonist gene variations predict the severity and progression of knee osteoartritis, Osteo. Cart., 18:S172 (2010).

Bukowski, J. et al., A49II-1RN Polymorphisms are associated with radiographic severity in osteoarthritis, osteo cartBUKOWSKI, J. et al., A49II-1RN Polymorphisms are associated with radiographic severity in osteoarthritis, Osteo. Cart., 16:S34 (2008).

(56) References Cited

OTHER PUBLICATIONS

Dam, E. B. et al., Increased urinary excretion of C-telopeptides of type II collagen (CTX-II) predicts cartilage loss over 21 months by MRI, Osteoarthritis and Cartilage, 17(3):384-389 (2009).

Kerkhof, H.J.M. et a., Large-scale meta-analysis of interleukin-1 beta and interleukin-1 receptor antagonist polymorphisms on risk of radiographic hip and knee osteoarthritis and severity of knee osteoarthritis, Osteoarthr. Cartil., 19:265-271 (2011).

Mummidi, S. et al., Evolution of Human and Non-human Primate CC Chemokine Receptor 5 Gene and mRNA, Jrnl. Biol. Chem., 275(25):18946-961 (2000).

Reker, D. et al., Extracellular Matrix Changes in Response to Sprifermin Studied in Ex Vivo Cultures of Aricular Cartilage, Abstract, Osteoarthritis and Cartilage, 206:A142-A143 (2015).

Reker, D. et al., Sprifermin (rhFGF18) modulates extracellular matrix turnover in cartilage explants ex vivo, J. Transl. Med., 15:1-12 (2017).

Wu, X. et al., 390 Progression or initiation of radiographic knee osteoarthritis and the interleukin-1 receptor antagonist gene: the Johnston county osteoarthritis project, Osteo. Cart., 18:S171-172 (2010).

Bay-Jensen, A.-C. et al., Elevated levels of CRPM, an inflammatory biomarker correlating with disease activity in RA, are prognostic of radiographic knee OA, Osteoarthritis and Cartilage, 25:S32 (2017).

Written Opinion for PCT/EP2018/076391, 6 pages (mailed Nov. 6, 2018).

* cited by examiner

A)

B)

A) WOMAC change from baseline in high and low CTX-II placebo subgroups

B) WOMAC change from baseline in high and low proC2 placebo subgroups

A)

B)

PBO = placebo arm
DLx = examples of active arms

MARKERS USEFUL IN ENRICHMENT STRATEGIES FOR THE TREATMENT OF OSTEOARTHRITIS

CROSS-REFERENCE TO RELATED APPLICATION

This application is the U.S. national stage application of International Patent Application No. PCT/EP2019/074003, filed Sep. 9, 2019.

The Sequence Listing for this application is labelled "Seq-List-replace-2.txt" which was created on Jul. 26, 2021 and is 21,000 bytes. The entire content of the sequence listing is incorporated herein by reference in its entirety.

FIELD OF INVENTION

The present invention relates to pharmacogenetics, more specifically to strategies involving markers associated with the clinical response to a compound before or during treatment of a cartilage disorder, such as osteoarthritis, with said compound. The present invention more particularly relates to the combination of Joint Space Width (JSW) measurements and level of specific proteins present in the blood, serum, synovial fluid or in the urine, which can be used in strategies such as patients' enrichment in clinical trials, patients' selection strategies before or during treatment or for adapting the treatment of a patient in the frame of treatments for cartilage disorder, such as osteoarthritis.

The invention further discloses diagnostic tools and kits based on the combination of JSW measurements and level of specific biomarkers. Thus, the invention can be used for predicting the response to a compound for the treatment of a cartilage disorder, before starting the treatment with said compound or during the treatment. The strategy could be used for selecting/identifying subjects to be treated by intra-articular administration of an active compound for treating a cartilage disorder and in patients' enrichment strategy. The use of these strategy, in diagnostics for instance, could result in increased benefit and reduced risk in subjects.

BACKGROUND OF THE INVENTION

Cartilage disorders broadly refer to diseases characterized by degeneration of metabolic abnormalities in the connective tissues which are manifested by pain, stiffness and limitation of motion of the affected body parts. These disorders can be due to pathology or can be the result of trauma or injury. Among others, cartilage disorders include osteoarthritis (OA), cartilage injury (inclusive sports injuries of cartilage and joint, and surgical injuries such as microfracture(s)). Mature cartilage has limited ability to repair itself, notably because mature chondrocytes have little potential for proliferation and due to the absence of blood vessels. In addition, cartilage is not well nitrified and has a low oxygen pressure. Replacement of damaged cartilage, in particular articular cartilage, caused either by injury or disease is a major challenge for physicians, and available surgical treatment procedures are considered not completely predictable and effective for only a limited time. Therefore, the majority of younger subjects either does not seek treatment or are counselled to postpone treatment for as long as possible. When treatment is required, the standard procedure is age dependent and varies between total joint replacement, transplantation of pieces of cartilage or marrow stimulating technique (such as microfracture). Microfracture is a common procedure that involves penetration of the subchondral bone to stimulate cartilage deposition by bone marrow derived stem cells. However, it has been shown that this technique does not repair sufficiently the chondral defect and the new cartilage formed is mainly fibrocartilage, resulting in inadequate or altered function and biomechanics. Indeed, fibrocartilage does not have the same durability and may not adhere correctly to the surrounding hyaline cartilage. For this reason, the newly synthesized fibrocartilage may breakdown more easily (expected time frame: 5-10 years).

For subjects with osteoarthritis, non-surgical treatment consists notably of physical therapy, lifestyle modification (e.g. increasing physical activity), supportive devices, oral and injected drugs (e.g. non-steroidal anti-inflammatory drugs), walking aids and medical symptom management. Once these treatments fail, surgery, such as joint replacement, is the main option for the subjects. Tibial or femoral osteotomies (cutting the bone to rebalance joint wear) may reduce symptoms, help to maintain an active lifestyle, and delay the need for total joint replacement. Total joint replacement can provide relief for the symptom of advanced osteoarthritis, but generally requires a change in a subject's lifestyle and/or activity level.

At that time, drug treatments on the market are mainly directed to pain relief. There is not yet commercially available treatment that restores or postpones the cartilage damages (see Lotz, 2010).

Fibroblast Growth factor 18 (FGF-18) is a member of the FGF family of proteins, closely related to FGF-8 and FGF-17. It has been shown that FGF-18 is a proliferative agent for chondrocytes and osteoblasts (Ellsworth et al., 2002; Shimoaka et al., 2002; Gigout et al., 2017). FGF-18 has been proposed for the treatment of cartilage disorder such as osteoarthritis and cartilage injury either alone (WO2008/023063) or in combination with hyaluronic acid (WO2004/032849).

Sprifermin, a truncated form of human FGF-18, is being investigated in clinical trials for treatment of both osteoarthritis and cartilage injury (see for instance NCT01033994, NCT00911469 and NCT01066871). The current dosing regimen for sprifermin is once weekly for 3 weeks (one treatment cycle), the drug being administered via intraarticular injections. This treatment cycle can be repeated. This dosing regimen has been described in WO2008/023063.

At that time, OA and cartilage injury treatments with FGF-18, during clinical trials, are provided to subjects without predictive information on the response (Lohmander et al., 2014; Dahlberg et al., 2016), i.e. without knowledge on whether the treatment will likely be highly effective, moderately effective or show only little or no effect. Currently, numerous treated subject population exhibit an intermediate/high response to treatment according to cartilage thickness, as measured by MRI technique and the WOMAC scores with sprifermin after at least one treatment cycle, however, some others either do not respond to said treatment (i.e. no or limited increase in cartilage thickness measured by MRI) or respond while presenting higher WOMAC score compared to control.

WO2014/023703 describes genetic markers (combination of SNPs IL-1RN rs9005 and IL-1RN rs315952) that are associated with the quality of the clinical response to treatment of cartilage disorder such as OA, cartilage injury or microfracture(s) with FGF-18. Such markers are useful for identifying, through genetic screening prior to the treatment, subgroups of subjects that are more likely to exhibit a particular response to treatment with FGF-18, such as a very good clinical response to treatment with FGF-18 or on the contrary those for whom the therapy may fail.

Knowledge on the type of clinical response of a subject to treatment can be used to select or stratify patients for clinical trials, select a therapy, optimize a therapy, such as selecting treatment with a compound as a first line therapy or adapting the dosing regimen. Such information will be clinically useful for the management of clinical trials or for the medical management of cartilage disorder, such as of OA and/or cartilage injury, in subjects. In addition, such predictive information may also be clinically useful to guide decisions on the dosing regimen.

There is a need to identify further markers helping in predicting placebo response, helping in clinical trial management, in optimizing therapy or in selecting a therapy, in order to provide a full range of solution for the subject to be treated or for the doctor looking for the best therapy for his patient.

SUMMARY OF THE INVENTION

As described herein, metabolic biomarkers, such as proC2 or CTX-II, combined with the physical marker JSW (joint space width) can be used in the detection, stratification, diagnosis and/or treatment of patients with osteoarthritis or cartilage disorders. The expression levels (or quantity) of at least one of these biomarkers (or combinations thereof) combined with the physical marker JSW can be used, for instance, to better classify patient or to detect patients to be included or at the contrary excluded from specific therapy.

The present invention is directed to a method of derisking a clinical trial or of determining placebo effect in a clinical trial (wherein said clinical trial is related to the treatment of a cartilage disorder in a subject with an active compound) or during a treatment with an active compound, the method comprising the steps of:
  a) Measuring the joint space width (JSW) in at least one knee of said subject,
  b) Predicting from the result of step a) the risk of placebo effect.

According to said method, the presence of a JSW higher than 3.5±2SD mm is predictive of placebo effect. On the contrary, the presence of a JSW lower than or equal to 3.5±2SD mm is predictive of no or low placebo effect.

The present invention is also directed to a method of derisking a clinical trial, wherein said clinical trial is related to the treatment of a cartilage disorder in a subject with an active compound, the method comprising the steps of:
  a) Determining, from a sample from said subject, the quantity of at least one of the biomarkers selected from the group consisting of CTX-II and/or ProC2;
  b) Measuring the joint space width (JSW) in at least one knee of said subject,
  c) Predicting from the result of steps a) and b) sensitivity of said subject to treatment with said active compound,
wherein steps a) and b) are performed in either order.

According to said method, the presence of higher than 350±2SD ng/mmol of CTX-II, or higher than 4.2±2SD ng/ml of ProC2 together with JSW higher than 3.5±2SD mm, is predictive of low or no sensitivity to treatment with an active compound. On the contrary, the presence of 1) lower than 350±2SD ng/mmol of CTX-II and/or, lower than 4.2±2SD ng/ml of ProC2 together with JSW lower than or equal to 3.5±2SD mm, 2) lower than 350±2SD ng/mmol of CTX-II and/or lower than 4.2±2SD ng/ml of ProC2 together with a JSW higher than 3.5±2SD mm or 3) higher than 350±2SD ng/mmol of CTX-II and/or higher than 4.2±2SD ng/ml of ProC2 together with a JSW lower than 3.5±2SD mm is predictive of sensitivity to treatment with an active compound.

Also described is a method for selecting a subject having a cartilage disorder for inclusion in or exclusion from treatment, or clinical trial, with an active compound, based on the likelihood of their sensitivity to said treatment, comprising the steps of:
  a) Determining, from a sample from said subject, the quantity of at least one of the biomarkers selected from the group consisting of CTX-II and/or ProC2 and measuring the joint space width (JSW) in at least one knee of said subject; wherein the quantity of at least one of these proteins and the width if the JSW are predictive about the subject's risk for being sensitive or not-sensitive to said treatment, and
  b) Selecting the sensitive subjects as being suitable for said treatment, or clinical trial.

According to said method, the presence of higher than 350±2SD ng/mmol of CTX-II, or higher than 4.2±2SD ng/ml of ProC2 together with JSW higher than 3.5±2SD mm, leads preferably to the exclusion of said subject from the treatment with an active compound. On the contrary, the presence of 1) lower than 350±2SD ng/mmol of CTX-II and/or, lower than 4.2±2SD ng/ml of ProC2 together with JSW lower than or equal to 3.5±2SD mm, 2) lower than 350±2SD ng/mmol of CTX-II and/or lower than 4.2±2SD ng/mL of ProC2 together with a JSW higher than 3.5±2SD mm or 3) higher than 350±2SD ng/mmol of CTX-II and/or higher than 4.2±2SD ng/ml of ProC2 together with a JSW lower than 3.5±2SD mm leads to the inclusion of said subject from the treatment with an active compound.

Also described is a kit comprising means for performing the method according to the invention and instructions for use.

Also encompassed is an active compound for use in the treatment of a subject having a cartilage disorder, characterized in that the subject presents 1), lower than 350±2SD ng/mmol of CTX-II and/or lower than 4.2±2SD ng/ml of ProC2 together with JSW lower than or equal to 3.5±2SD mm, 2) lower than 350±2SD ng/mmol of CTX-II and/or lower than 4.2±2SD ng/ml of ProC2 together with a JSW higher than 3.5±2SD mm or 3) higher than 350±2SD ng/mmol of CTX-II and/or higher than 4.2±2SD ng/ml of ProC2 together with a JSW lower than 3.5±2SD mm.

The present invention is also directed to a method for treating a subject with an active compound having a cartilage disorder, comprising the following steps:
  a) Determining, from a sample from said subject, the quantity of at least one of the biomarkers selected from the group consisting of CTX-II and/or ProC2 and measuring the joint space width (JSW) in at least one knee of said subject, wherein said quantities and widths are predictive about the subject's risk for being sensitive to a treatment with said active compound
  b) Selecting the subject having
    i. Lower than 350±2SD ng/mmol of CTX-II, and/or lower than 4.2±2SD ng/ml of ProC2 together with JSW lower than or equal to 3.5±2SD mm,
    ii. lower than 350±2SD ng/mmol of CTX-II and/or lower than 4.2±2SD ng/ml of ProC2 together with a JSW higher than 3.5±2SD mm or
    iii. higher than 350±2SD ng/mmol of CTX-II and/or higher than 4.2±2SD ng/ml of ProC2 together with a JSW lower than 3.5±2SD mm.
  c) Administering intraarticularly said active compound to said selected subject.

In particular embodiments of the present invention as a whole, i.e. in any of the methods or uses mentioned herein, the subject has a cartilage disorder selected from the group consisting of osteoarthritis, cartilage injury, fractures affecting joint cartilage or surgical procedures with impact on joint cartilage (e.g. Microfracture) and the active compound can be selected for instance form the group consisting of FGF-18 compound, BMP-2, BMP-7, GDF-5, FGFβ, FGF-9, SOX-9 enhancers, TGFβ, Wnt inhibitors, anti-MMP13 inhibitors, anti-ADAMTS5 inhibitors, calcitonin and any variants or fusion proteins thereof.

It is to be understood that in any of the methods or uses mentioned herein, before determining the quantity of at least one of the proteins, it is needed to obtain a sample (or a test sample) of said subject, via for instance blood, serum, synovial fluid or urine collecting. Further, it is also to be understood that any of the methods or uses mentioned herein are performed in vitro, and not on the animal or human body.

Definitions

The term "FGF-18 compound" or "FGF-18", as used herein, is intended to be a protein maintaining at least one biological activity (e.g. increase in osteoblastic activity, see WO98/1664, or in cartilage formation, see WO2008/023063) of the wildtype human FGF-18 protein. FGF-18 may be native (SEQ ID NO: 1), in its mature form (corresponding to the amino acid sequence from residue 28 (Glu) to residue 207 (Ala) of SEQ ID NO: 1), or a truncated form thereof such as sprifermin (as shown in SEQ ID NO:2; with amino acid residues 2 to 170 of SEQ ID NO:2 corresponding to amino acid residues 28 to 196 of SEQ ID NO:1). The term "FGF-18 compound" also includes variants or mutants of the native, mature form, or truncated forms of FGF-18, as well as fusion proteins comprising a (biologically) active FGF-18 moiety coupled to a heterologous protein or a chemical compound (such as those disclosed in EP17192467.3 patent family). In such fusion proteins, the FGF-18 moiety can be the native, mature form, or truncated forms of the FGF-18 protein or variants or mutants thereof.

The term "BMP-2", as used herein, is a protein inducing matrix synthesis and promoting cartilage repair as well as playing a critical role in the differentiation of osteo-progenitor cells into osteoblasts, thus promoting bone and cartilage formation (Deng et al., 2018). The full-length native form of the human BMP-2 is represented in SEQ ID NO. 6. One of the recombinant forms of BMP-2 protein is known as Dibotermin alfa. This term "BMP-2" also includes variants thereof or fusion proteins comprising a BMP-2 moiety The term "BMP-7", as used herein, is a protein known for its osteogenic properties, shown to have a strong anabolic effect on cartilage by stimulating synthesis of cartilage matrix components and increasing proteoglycan and collagen synthesis (Deng et al., 2018). The full-length native form of the human BMP7 is represented in SEQ ID NO. 7. One of the recombinant forms of BMP-2 protein is known as eptotermin alfa. This term also includes variants thereof or fusion proteins comprising a BMP-7 moiety The term "GDF-5", also known as LAP-4 or radotermin, as used herein, is a protein, having among others, stimulatory effects on the synthesis of matrix in human articular chondrocytes cultured in vitro, from both healthy subjects as well as OA patients (Parrish et al., 2017). The full-length native form of the human GDF-5 is represented in SEQ ID NO. 8. This term also includes variants thereof or fusion proteins comprising a GDF-5 moiety.

The term "FGFβ" or "FGF-2", as used herein, is a protein known in cartilage repair. It was also shown to stimulate the proliferation of chondrocytes in immature rabbits (Ameye and Young, 2006). The full-length native form of the human FGF-2 is represented in SEQ ID NO. 9. One of the recombinant forms of FGFβ protein is known as trafermin. This term also includes variants thereof or fusion proteins comprising an FGFβ moiety.

The term "FGF-9", as used herein, is a protein known to delay articular cartilage degradation in OA subject, while having a rather negative impact on osteophyte formation (Zhou et al., 2016). The full-length native form of the human FGF-9 is represented in SEQ ID NO. 10. This term also includes variants thereof or fusion proteins comprising a FGF-9 moiety.

The term "TGF-β", as used herein, is a protein TGF-beta belonging to the TGF-beta family having a crucial role in cartilage maintenance. TGF-beta has been shown as an enhancer of cartilage (Wang 2014). This term also includes variants thereof or fusion proteins comprising a TGF-β moiety.

The term "SOX-9" enhancers. as used herein, is intended to be a compound enhancing the production of SOX9. Indeed, SOX9 is a transcription factor shown to be essential for cartilage extracellular matrix (ECM) formation.

The term "calcitonin" as used herein, is more especially the salmon calcitonin type, a 32-amino-acid peptide (SEQ ID NO. 5), which demonstrated to have protective activity on both bone and cartilage.

The term "Wnt inhibitors" as used herein, is intended to be a compound interfering with WNT pathway.

The term "anti-MMP13 inhibitors" as used herein is intended to be a compound inhibiting the activity of the matrix metalloproteinase 13 (MMP13). MMP13 is one of the key collagen type II degrading enzymes.

The term "anti-ADAMTS4 or 5 inhibitors" as used herein, is intended to be compound inhibiting the enzymatic activity of a disintegrin and metalloproteinase with thrombospondin motifs 4 or 5 (ADAMTS4 or ADAMTS5).

The term "biomarker" or "protein marker" are used interchangeably. In the context of the present invention they are peptides or proteins. A "prognostic biomarker" is informative about the subject condition, including and not limited to disease evolution, disease severity or disease outcome, regardless of any therapy. A "predictive biomarker" is informative about the effect of a received therapy, including, but not limited to efficacy and safety outcome. The prognostic and predictive definitions are not mutually exclusive thus a biomarker can be both prognostic and predictive. The quantity of biomarker or the expression level of biomarker is herein expressed as nmol, umol, mmol, ng, µg, mg or g of a given protein. Said quantity or level can be expressed as absolute value (e.g. 10 ng or 2 µg) or as concentration (e.g. 10 ng/ml, 2 µg/mL, 10 ng/mmol or 2 µg/mmol).

The term "metabolic biomarker" refers to biomarkers such as, but not limited to, CTX-II, ProC2, PIIANP, C2M, ARGS and AGNx1. More specifically the term "metabolic biomarker" refers to biomarkers of cartilage metabolism, i.e. collagen and aggrecan turnover such degradation and/or synthesis of cartilage matrix components. Different collagen and aggrecan biomarkers have been described (Karsdal et al., 2016).

The term "CTX-II" or "CTXII" refers to C-terminal telopeptide of type II collagen. See SEQ ID NO. 1. It is biomarker of collagen type II degradation being part of osteoarthritis (see for instance Duclos et al., 2010).

The term proC2 refers to a neo-epitope of Collagen type II generated during synthesis of Collagen type II, with sequence QDVRQP recognised as epitope in proC2 assay: ProC2 is a biomarker of cartilage formation (type II collagen formation) assay. See SEQ ID NO. 2. ProC2 is associated with capacity for repair and may be valuable tool for the identifying patients with cartilage-driven disease. ProC2 has been tested the biomarker in clinical samples preclinical studies (see e.g. Gudmann et al., 2016; Munk et al., 2016; Gudmann et al., 2014).

The term PIIANP refers to a propeptide of Collagen type II: Type IIA procollagen contains an N-terminal 69 amino acid, cysteine-rich globular domain that is encoded by exon 2 of the Collagen type II gene. Type IIA procollagen has been found to be synthesized by osteoarthritic chondrocytes in diseased cartilage and may serve as a specific arthritis biomarker that reflects an attempt by the chondrocytes to repair diseased cartilage (Valdes et al, 2014).

The term C2M refers to a serological type II collagen degradation neoepitope linked to cartilage degradation. C2M is an interhelical fragment for type II collagen generated by MMP. The biomarker has been described to be associated with drug response, pain measures and radiographic severity. (Valdes et al. 2014).

The term ARGS refers to a neoepitope generated during Aggrecan degradation. The assay detects Aggrecan degradation products in serum and synovial fluid. ARGS levels are linked to progression in cartilage disorders (Struglics et al., 2011; Struglics et al., 2015).

The term AGNx1 relates to an assay that detects another neoepitope generated during Aggrecan degradation.

In relation to the biomarkers, the term "quantity" or "expression level" can be used interchangeably. The term "physical marker" refers to the joint space width (JSW) and its assessment in the context of the present invention.

the term "SD" means standard deviation and is linked to the usual deviations of any validation assays/systems.

"Cartilage disorder", as used herein, encompasses disorders resulting from damages due to injury, such as traumatic injury, chondropathy or arthritis. Examples of cartilage disorders that may be treated by the administration of the compounds described herein include but are not restricted to arthritis, such as osteoarthritis, cartilage injury, fractures affecting joint cartilage or surgical procedures with impact on joint cartilage (e.g. Microfracture). Degenerative diseases/disorders of the cartilage or of the joint, such as chondrocalcinosis, polychondritis, relapsing polychondritis, ankylosing spondylitis or costochondritis are also encompassed by this wording. The International Cartilage Repair Society has proposed an arthroscopic grading system to assess the severity of the cartilage defect: grade 0: (normal) healthy cartilage, grade 1: the cartilage has a soft spot or blisters, grade 2: minor tears visible in the cartilage, grade 3: lesions have deep crevices (more than 50% of cartilage layer) and grade 4: the cartilage tear exposes bone the underlying (subchondral) (see for instance page 13 of www.cartilage.org/_files/content-management/ICRS_evaluation.pdf).

The term "Osteoarthritis" is used to intend the most common form of arthritis. The term "osteoarthritis" encompasses both primary osteoarthritis and secondary osteoarthritis (see for instance The Merck Manual, 17$^{th}$ edition, page 449). The most common way of classifying/grading osteoarthritis is the use of the Kellgren-Lawrence radiographic grading scale (see table below). Osteoarthritis may be caused by the breakdown of cartilage. Bits of cartilage may break off and cause pain and swelling in the joint between bones. Over time, the cartilage may wear away entirely, and the bones will rub together. Osteoarthritis can affect any joint but usually concerns hands and weight-bearing joints such as hips, knees, feet, and spine. In a preferred example, the osteoarthritis may be knee osteoarthritis or hip osteoarthritis. Osteoarthritis is one of the preferred cartilage disorders that can be treated by administering the compounds according to the present invention.

Kellgren-Lawrence Radiographic Grading Scale (KL) of Osteoarthritis is described as follow:

| Grade of Osteoarthritis | Description |
| --- | --- |
| 0-None | No radiographic findings of osteoarthritis |
| 1-Doubtful | Doubtful narrowing of joint space and possible osteophytic lipping |
| 2-Minimal | Definite osteophytes, definite narrowing of joint space |
| 3-Moderate | Moderate multiple osteophytes, definite narrowing of joints space, some sclerosis and possible deformity of bone contour |
| 4-Severe | Large osteophytes, marked narrowing of joint space, severe sclerosis and definite deformity of bone contour |

Grades 1 and 2 can be considered as less severe forms of the disease, whereas grades 3 and 4 can be considered as more severe forms of the disease.

The term "cartilage injury" as used herein is a cartilage disorder or cartilage damage resulting notably from a trauma. Cartilage injuries can occur notably after traumatic mechanical destruction, notably further to an accident or surgery (for instance microfracture surgery). This term "cartilage injury" also includes chondral or osteochondral fracture, damage to meniscus, and the term microfracture. Also considered within this definition is sport-related injury or sport-related wear of tissues of the joint.

"WOMAC total scores" or "WOMAC scores" ("WOMAC" for "Western Ontario and McMaster Universities Osteoarthritis Index") measure pain (WOMAC pain score), function (WOMAC function score) and stiffness (WOMAC stiffness score). When applied to assessing of pain and dysfunction associated with cartilage injury, it consists of a questionary containing 24 items divided into 3 subscales (5 items for Pain, 2 items for Stiffness and 17 items for Physical Function) (see Bellamy et al., 1988; Wolfe, 1999). It is a well-known instrument, widely used notably in assessment of the OA severity.

In order to evaluate cartilage repair, cartilage volume measurements were performed through magnetic resonance imaging (MRI) measurements, including Lateral volume of cartilage (also referred as LFTC), Medial volume of cartilage (also referred as MFTC), Total volume of cartilage (also referred as LFTC+MFTC) and new total average cartilage thickness.

The term "thin" cartilage, refers to a cartilage having a JSW lower than or equal to 3.5±2SD mm.

The term "thick" cartilage, refers to a cartilage having a JSW higher than 3.5±2SD mm.

The term "baseline" means before treatment (i.e. at study entry). It refers notably to clinical variables, such as, but not limited to, the cartilage volume and WOMAC total score of one given subject at study entry (i.e. before treatment with the active compound or placebo).

The term "subject" or "patient" refers to both human and non-human animals. The term non-human comprises mammals such as rodents (including mice), rabbits, cats, dogs, horses, cows, sheep, or primates.

"Sensitives" are subjects that exhibit a response to treatment of a cartilage disorder with an active compound. Preferably, sensitive subjects (or subjects showing/likely to show sensitivity/response to treatment) exhibit notably a higher increase in total cartilage thickness and/or cartilage volume than placebo treated subjects, i.e. they show cartilage repair. In addition, sensitive subjects exhibit at least similar improvement in WOMAC total scores than placebos. The terms "sensitive" (including both "good-sensitive" and "intermediate-sensitive") and "non-sensitive" (including "Low-sensitive") refer to the different groups of subjects depending notably on the increase of the cartilage volume following treatment with an active compound. Good-sensitive subjects display a high response (i.e. high cartilage repair) to treatment with an active compound, intermediate-sensitive display an intermediate response (i.e. intermediate cartilage repair) to treatment with said active compound, and non-sensitives display no or low response to treatment with said active compound. Good-sensitive subjects have preferably a similar improvement in WOMAC total score than placebos. Conversely non-responders have significantly smaller improvement in WOMAC total score than placebos.

More particularly, the terms "Intermediate-sensitives", "good-sensitives", "Non-sensitives", "intermediate responders", "good responders" and "non-responders" (including low-responders) relate to the different groups of subjects depending on the increase of the cartilage volume and improvement of WOMAC total score, following treatment with an active compound.

The proposed criteria for assessing sensitivity/response can be selected from one or more of the following (but not limited to):

1. Positive cartilage increase compared to baseline,
2. Cartilage increase change significantly higher than change in placebo (e.g. as tested with a linear model adjusting for BMI, KL grade, sex and age and with alpha=5%),
3. WOMAC score improvement, i.e. diminution, (e.g. more than 5 points reduction) compared to baseline,
4. WOMAC score change not significantly higher than change in placebo (e.g. as tested with a linear model adjusting for BMI, KL grade, sex and age and with alpha=5%).

The "response", or "sensitivity" to an active compound treatment for a cartilage disorder is to be understood as at least after 1 year or even better 2 years after the first injection and measured as 1) increase of cartilage volume, measured owing to MRI or X-Ray for instance, 2) decrease of WOMAC total scores, or 3) changes in WOMAC total scores not significantly higher than those from placebos (refer also to the definition of "sensitive").

The term "placebo effect" as used herein is to be understood as changes compared to baseline by the placebo itself (e.g. dilution of inflammatory components in synovial fluid), due to the contextual influences (e.g. the procedure of an intraarticular injection by a medical doctor) and by patients' expectations. The term "Low placebo effect" refers to a response magnitude comparable to the one at baseline, within the standard deviation of the assessment method.

The term "storage device", as used herein, is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media.

As used herein, the term "stored" refers to a process for encoding information on the storage device. Those skilled in the art can readily adopt any of the presently known methods for recording information on known media to generate manufactures comprising expression level information.

DETAILED DESCRIPTION OF THE INVENTION

There is a need to 1) predict placebo response in subjects having cartilage disorder, as well as 2) predict the clinical efficacy (notably with regards to cartilage repair) of an active compound treatment for the treatment of subjects having a cartilage disorder, such as osteoarthritis, cartilage injury, fractures affecting joint cartilage or surgical procedures with impact on joint cartilage (e.g. Microfracture). To optimize the management of clinical trials or to optimize the treatment of said subjects, it is important to identify markers that could be used as predictors of 1) the placebo response and/or 2) the response of a given subject to the active compound treatment, notably with regard to cartilage repair. Such predictive biomarkers may be used to identify 1) groups of subjects at risk of presenting placebo effect and/or 2) high-risk groups either being less-sensitives or on the contrary sensitive (e.g. intermediate or good sensitive) or even high-sensitive to the treatment. For instance, if one subject having osteoarthritis is known to be at high risk for intermediate-response (or for being intermediate-sensitive) to the treatment, the physician may decide to adapt the dose regimen, in order to e.g. higher the dose of the active compound to be administered to said subject and/or in order to administer the dug on a longer period of time. Such predictive information may be clinically useful to guide medical decisions, notably on the dosing regimen or the length of a treatment to be applied to one patient or on the timing of joint replacement surgery when needed (for instance if an active compound treatment is predicted to be less efficient).

The surprising finding of the present invention is based on different studies aimed at identifying potential markers associated with the administration of different active compounds. The biomarkers used in these studies were composed of numerous protein biomarkers. The physical marker was the JSW measurement. The association between the protein markers and/or physical marker and the clinical response variables was assessed. The rationale behind this type of analysis was to identify combination of markers that could be predictive of 1) placebo response and/or 2) the clinical outcome (notably with regard to cartilage repair), for a subject to be treated with an active compound such as an FGF-18 compound, BMP-2, BMP-7, GDF-5, FGFβ, FGF-9, SOX-9 enhancers, TGFβ, Wnt inhibitors, anti-MMP13 inhibitors, anti-ADAMTS4 or 5 inhibitors, calcitonin and any variants or fusion proteins thereof. In particular, it was surprisingly found that 1) JSW measurements could be used to predict placebo effect and 2) protein biomarkers together with JSW measurement could be used to stratify and target specific subject populations.

Different markers demonstrated change in response to active compound therapies or shown changes in outcomes (i.e. cartilage thickness or volume, WOMAC scores) by applying criteria for high and low values. Examples are C1M, C3M and hs-CRP. The inventors have surprisingly found an association with certain metabolic proteins in combination with a physical marker and outcome (e.g. cartilage repair). Of special interest are the proteins CTX-II and ProC2. It is noted that although only CTX-II and/or ProC2 are specifically described herein, other metabolic biomarkers such as PIIANP, C2M, ARGS or AGNx1 could be used. Based on the teaching of the present invention, it would then be routine matter for the skilled person to find the thresholds for each of these biomarkers. These proteins have been described in the literature, as being possibly related to osteoarthritis. For instance, CTX-II and ProC2 could be considered as metabolic biomarkers (Bay-Jensen, 2016).

It has been surprisingly found by the present inventors that for a given subject (having a cartilage disorder) presenting a JSW higher than 3.5±2SD mm, whatever the level of biomarkers, the placebo response was high: there was a strong placebo effect among these subjects possibly biasing the results of clinical trials and later on possibly biasing treatment by hiding the actual lack of effect of a given active compound. It has been also surprisingly found that when the quantity of metabolic biomarkers such as CTX-II and/or ProC2 is/are decreased, and the JSW is below a certain limit, this combination was associated with a better response to treatment with an active compound, such as FGF-18 compound, BMP-2, BMP-7, GDF-5, FGFβ, FGF-9, SOX-9 enhancers, TGFβ, Wnt inhibitors, anti-MMP13 inhibitors, anti-ADAMTS4 or 5 inhibitors, calcitonin and any variants or fusion protein thereof, in subjects afflicted with a cartilage injury. Such a subject is called good-sensitive (or good-responder). To the opposite, it has also surprisingly been found by the present inventors that when the quantity of CTX-II and/or ProC2 is/are increased, and the JSW is above a certain limit, this was associated with an absence of, or low, response to treatment with an active compound (i.e. low-sensitivity or non-sensitivity to treatment with said active compound) in subjects afflicted with cartilage disorder. Such a subject is called no-sensitive (or non-responder). Alternatively, 1) when the quantity of metabolic biomarkers such as CTX-II and/or ProC2 is/are decreased, and the JSW is above a certain limit, or 2) when the quantity of metabolic biomarkers such as CTX-II and/or ProC2 is/are increased, and the JSW is below a certain limit, this may be associated with intermediate response, i.e. the subject will be intermediate-sensitive (or intermediate-responder).

Therefore, it is a finding of the present invention that metabolic biomarkers such as CTX-II and/or ProC2 in combination with the physical marker JSW can be used as predictive markers of responsiveness of one subject to an active compound treatment, such as FGF-18 compound, BMP-2, BMP-7, GDF-5, FGFβ, FGF-9, SOX-9 enhancers, TGFβ, Wnt inhibitors, anti-MMP13 inhibitors, anti-ADAMTS4 or 5 inhibitors, calcitonin and any variants or fusion protein thereof. Preferably, the subject has a cartilage disorder, such as osteoarthritis, cartilage injury, fractures affecting joint cartilage or surgical procedures with impact on joint cartilage (e.g. Microfracture). In a particular embodiment, the subject will be predicted to be no-sensitive to an active compound treatment if the quantity of CTX-II is higher than 350±2SD ng/mmol CTX-II (>240-260% of normal mean) and/or the quantity of ProC2 is higher than 4.2±2SD ng/ml (>120-280% of normal mean) and if the JSW is higher than 3.5±2SD mm. On the contrary, the subject will be predicted to be good-sensitive to an active compound treatment if the quantity of CTX-II is lower than 350±2SD ng/mmol and/or the quantity of ProC2 is lower than 4.2±2SD ng/ml and if the JSW lower than or equal to 3.5±2SD mm. The subject will be predicted to be intermediate-sensitive to an active compound treatment if 1) the quantity of CTX-II is lower than 350±2SD ng/mmol and/or the quantity of ProC2 is lower than 4.2±2SD ng/ml and the JSW higher than 3.5±2SD mm or 2) if the quantity of CTX-II is higher than 350±2SD ng/mmol and/or the quantity of ProC2 is higher than 4.2±2SD ng/ml and the JSW lower than 3.5±2SD mm.

The present invention is therefore directed to a method of derisking a clinical trial or of determining placebo effect in a clinical trial (wherein said clinical trial is related to the treatment of a cartilage disorder in a subject with an active compound) or during a treatment with an active compound, the method comprising the steps of:
a) Measuring the joint space width (JSW) in at least one knee of one subject, and
b) Predicting from the result of step a) the risk of placebo effect for said subject.

According to said method, the presence of a JSW higher than 3.5±2SD mm is predictive of placebo effect. On the contrary, the presence of a JSW lower than or equal to 3.5±2SD mm is predictive of no or low placebo effect. From said prediction:
For clinical trial, the clinician can easily classify the subjects depending on their likelihood to present a placebo effect or not.
For treatment of cartilage disorder the doctor can easily determine if a subject is likely to be sensitives to a given active compound treatment (including both intermediate-sensitives and high-sensitives).

Alternatively, the present invention is directed to a method of derisking a clinical trial or of determining placebo effect in a subject in a clinical trial (wherein said clinical trial is related to the treatment of a cartilage disorder in a subject with an active compound) or during a treatment with an active compound, the method comprising the steps of:
a) Determining, from a sample from said subject, the quantity of at least one of the biomarkers selected from the group consisting of CTX-II and/or ProC2;
b) Measuring the joint space width (JSW) in at least one knee of said subject, and c) Predicting from the result of steps a) and b) the risk of placebo effect, wherein steps a) and b) are performed in either order.

Before determining the quantity of at least one of the biomarkers, it is needed to obtain a sample (or biological sample or test sample) of said subject, for instance by blood, serum, synovial fluid or urine collecting. Thus, the present invention is directed to a method of determining placebo effect in a subject in a clinical trial (wherein said clinical trial is related to the treatment of a cartilage disorder in a subject with an active compound) or during a treatment with an active compound, the method comprising the steps of:
  a) Obtaining a sample from said patient and determining, from said sample, the quantity of at least one of the biomarkers selected from the group consisting of CTX-II and/or ProC2;
  b) Measuring the joint space width (JSW) in at least one knee of said subject, and
  c) Predicting from the result of steps a) and b) the risk of placebo effect for said subject, wherein steps a) and b) are performed in either order.

According to said method, the presence of higher than 350±2SD ng/mmol of CTX-II (>240-260% of normal mean) and/or higher than 4.2±2SD ng/ml of ProC2 (>120-280% of normal mean) together with a JSW higher than 3.5±2SD mm is predictive of placebo effect. Similarly, the presence of either 1) lower than 350±2SD ng/mmol of CTX-II and/or lower than 4.2±2SD ng/ml of ProC2 together with a JSW higher than 3.5±2SD mm, or 2) higher than 350±2SD ng/mmol of CTX-II and/or higher than 4.2±2SD ng/ml of ProC2 together with a JSW lower than 3.5±2SD mm is predictive of placebo effect. On the contrary, the presence of lower than 350±2SD ng/mmol of CTX-II and/or lower than 4.2±2SD ng/ml of ProC2 together with a JSW lower than or equal to 3.5±2SD mm is predictive of no or low placebo effect. From said prediction:
  For clinical trial, the clinician can easily classify the subjects depending on their likelihood to present a placebo effect or not.
  For treatment of cartilage disorder the doctor can easily determine if a subject is likely to be sensitives to a given active compound treatment (including both intermediate-sensitives and high-sensitives).

The present invention is also directed to a method of derisking a clinical trial, wherein said clinical trial is related to the treatment of a cartilage disorder in a subject with an active compound, the method comprising the steps of:
  c) Determining, from a sample from said subject, the quantity of at least one of the biomarkers selected from the group consisting of CTX-II and/or ProC2,
  d) Measuring the joint space width (JSW) in at least one knee of said subject, and
  e) Predicting from the result of steps a) and b) the response of said subject to treatment with said active compound, wherein steps a) and b) are performed in either order.

Before determining the quantity of at least one of the biomarkers, it is needed to obtain a sample (or biological sample or test sample) of said subject, for instance by blood, serum, synovial fluid or urine collecting. Thus, the present invention is directed to a method of derisking a clinical trial, wherein said clinical trial is related to the treatment of a cartilage disorder in a subject with an active compound, the method comprising the steps of:
  a) Obtaining a sample from said patient and determining, from said sample, the quantity of at least one of the biomarkers selected from the group consisting of CTX-II and/or ProC2,
  b) Measuring the joint space width (JSW) in at least one knee of said subject, and
  c) Predicting from the result of steps a) and b) the response of said subject to treatment with said active compound, wherein steps a) and b) are performed in either order.

According to said method, the presence of higher than 350±2SD ng/mmol of CTX-II (>240-260% of normal mean) and/or higher than 4.2±2SD ng/ml of ProC2 (>120-280% of normal mean) together with a JSW higher than 3.5±2SD mm is predictive of no or low response (i.e. no- or low-sensitivity) to treatment with an active compound. The subject will thus be predicted to be no-sensitive (or non-responder). On the contrary, the presence of lower than 350±2SD ng/mmol of CTX-II and/or lower than 4.2±2SD ng/ml of ProC2 together with a JSW lower than or equal to 3.5±2SD mm is predictive of good response (i.e. good sensitivity) to treatment with an active compound. The subject will thus be predicted to be good sensitive to treatment with said active compound (i.e. he will be a good responder). The presence of either 1) lower than 350±2SD ng/mmol of CTX-II and/or lower than 4.2±2SD ng/ml of ProC2 and a JSW higher than 3.5±2SD mm, or 2) higher than 350±2SD ng/mmol of CTX-II and/or higher than 4.2±2SD ng/ml of ProC2 and a JSW lower than 3.5±2SD mm, is predictive of intermediate response (i.e. intermediate-sensitivity) to treatment with an active compound. The subject will thus be predicted to be intermediate-sensitive to treatment with said active compound (i.e. he will be an intermediate-responder). From said prediction, the doctor can easily select only those subjects that are predicted to be sensitives to a given active compound treatment, including both intermediate-sensitives and good-sensitives.

The present application also encompasses a method for selecting a subject having a cartilage disorder for inclusion in or exclusion from treatment, or clinical trial, with an active compound, based on the likelihood of their sensitivity to said treatment, comprising the steps of:
  a) Determining, from a sample from said subject, the quantity of at least one of the biomarkers selected from the group consisting of CTX-II and/or ProC2 and measuring the joint space width (JSW) in at least one knee of said subject; wherein the quantity of at least one of these proteins and the width if the JSW are predictive about the subject's risk for being sensitive or not-sensitive to said treatment, and
  b) Selecting the intermediate-sensitive and/or good-sensitive subjects as being suitable for said treatment or clinical trial.

Before determining the quantity of at least one of the biomarkers, it is needed to obtain a sample (or biological sample or test sample) of said subject, for instance by blood, serum, synovial fluid or urine collecting. Thus, the present invention is directed to a method for selecting a subject having a cartilage disorder for inclusion in or exclusion from treatment, or clinical trial, with an active compound, based on the likelihood of their sensitivity to said treatment, comprising the steps of:
  a) Obtaining a sample from said patient and determining, from said sample, the quantity of at least one of the biomarkers selected from the group consisting of CTX-II and/or ProC2 and measuring the joint space width (JSW) in at least one knee of said subject; wherein the quantity of at least one of these proteins and the width if the JSW are predictive about the subject's risk for being sensitive or not-sensitive to said treatment, and b) Selecting the intermediate-sensitive and/or good-sensitive subjects as being suitable for said treatment or clinical trial.

According to said method, the subject presenting higher than 350±2SD ng/mmol of CTX-II and/or higher than 4.2±2SD ng/mL of ProC2 together with a JSW higher than 3.5±2SD mm will preferably be excluded from treatment with an active compound. To the contrary, the subject presenting lower than 350±2SD ng/mmol of CTX-II and/or lower than 4.2±2SD ng/ml of ProC2 together with a JSW lower than or equal to 3.5±2SD mm will preferably be included (i.e. they will preferably be selected) for the treatment with an active compound. The subject presenting either 1) lower than 350±2SD ng/mmol of CTX-II and/or lower than 4.2±2SD ng/ml of ProC2 together with a JSW higher than 3.5±2SD mm, or 2) higher than 350±2SD ng/mmol of CTX-II and/or higher than 4.2±2SD ng/ml of ProC2 together with a JSW lower than 3.5±2SD mm, will preferably be also included for the treatment with an active compound, possibly with an alternative dosing regimen according to which the dose of the active compound is increased and/or the active compound is administered for a longer treatment period.

Alternatively, herein described is a method for treating a subject having a cartilage disorder with an active compound, comprising the following steps:

a) Determining, from a sample from said subject, the quantity of at least one of the biomarkers selected from the group consisting of CTX-II and/or ProC2 and measuring the joint space width (JSW) in at least one knee of said subject, wherein said quantities and width are predictive about the subject's risk for being good sensitive to a treatment with said active compound, b) Selecting the subject having:
   i. Lower than 350±2SD ng/mmol of CTX-II, and/or lower than 4.2±2SD ng/ml of ProC2 and JSW lower than or equal to 3.5±2SD mm,
   ii. lower than 350±2SD ng/mmol of CTX-II and/or lower than 4.2±2SD ng/ml of ProC2 together with a JSW higher than 3.5±2SD mm or
   iii. higher than 350±2SD ng/mmol of CTX-II and/or higher than 4.2±2SD ng/ml of ProC2 together with a JSW lower than 3.5±2SD mm, and c) Administering said active compound to said selected subject.

Before determining the quantity of at least one of the biomarkers, it is needed to obtain a sample (or biological sample or test sample) of said subject, for instance by blood, serum, synovial fluid or urine collecting. Thus, the present invention is directed to a method for treating a subject having a cartilage disorder with an active compound, comprising the following steps:

a) Obtaining a sample from said patient and determining, from said sample, the quantity of at least one of the biomarkers selected from the group consisting of CTX-II and/or ProC2 and measuring the joint space width (JSW) in at least one knee of said subject, wherein said quantities and width are predictive about the subject's risk for being good sensitive to a treatment with said active compound, b) Selecting the subject having:
   i. Lower than 350±2SD ng/mmol of CTX-II, and/or lower than 4.2±2SD ng/ml of ProC2 and JSW lower than or equal to 3.5±2SD mm,
   ii. lower than 350±2SD ng/mmol of CTX-II and/or lower than 4.2±2SD ng/ml of ProC2 together with a JSW higher than 3.5±2SD mm or
   iii. higher than 350±2SD ng/mmol of CTX-II and/or higher than 4.2±2SD ng/ml of ProC2 together with a JSW lower than 3.5±2SD mm, and c) Administering said active compound to said selected subject.

Although the intermediate sensitive subjects (having either 1) lower than 350±2SD ng/mmol of CTX-II and/or lower than 4.2±2SD ng/ml of ProC2 together with a JSW higher than 3.5±2SD mm or 2) higher than 350±2SD ng/mmol of CTX-II and/or higher than 4.2±2SD ng/ml of ProC2 together with a JSW lower than 3.5±2SD mm) can be treated with the same dosing regimen as the good-sensitive subjects (having Lower than 350±2SD ng/mmol of CTX-II, and/or lower than 4.2±2SD ng/ml of ProC2 and JSW lower than or equal to 3.5±2SD mm), these subjects may have better benefit with an alternative dosing regimen.

Therefore, also herein described is a method for treating a subject having a cartilage disorder with an active compound, comprising the following steps:

a) Determining, from a sample from said subject, the quantity of at least one of the biomarkers selected from the group consisting of CTX-II and/or ProC2 and measuring the joint space width (JSW) in at least one knee of said subject, wherein said quantities and width are predictive about the subject's risk for being intermediate sensitive to a treatment with said active compound, b) Selecting the subject having:
   i. Lower than 350±2SD ng/mmol of CTX-II, and/or lower than 4.2±2SD ng/ml of ProC2 and JSW higher than to 3.5±2SD mm, or
   ii. higher than 350±2SD ng/mmol of CTX-II and/or higher than 4.2±2SD ng/ml of ProC2 and of a JSW lower than 3.5±2SD mm, and c) Administering said active compound to said selected subject according to an alternative dosing regimen according to which the dose of the active compound is increased, and/or the active compound is administered for a longer treatment period compared to the usual dosing regimen for said active compound.

Before determining the quantity of at least one of the biomarkers, it is needed to obtain a sample (or biological sample or test sample) of said subject, for instance by blood, serum, synovial fluid or urine collecting. Thus, the present invention is directed to a method for treating a subject having a cartilage disorder with an active compound, comprising the following steps:

a) Obtaining a sample from said patient and determining, from said sample, the quantity of at least one of the biomarkers selected from the group consisting of CTX-II and/or ProC2 and measuring the joint space width (JSW) in at least one knee of said subject, wherein said quantities and width are predictive about the subject's risk for being intermediate sensitive to a treatment with said active compound, b) Selecting the subject having:
   i. Lower than 350±2SD ng/mmol of CTX-II, and/or lower than 4.2±2SD ng/ml of ProC2 and a JSW higher than 3.5±2SD mm, or
   ii. higher than 350±2SD ng/mmol of CTX-II and/or higher than 4.2±2SD ng/mL of ProC2 and a JSW lower than 3.5±2SD mm, and c) Administering said active compound to said selected subject according to an alternative dosing regimen according to which the dose of the active compound is increased, and/or the active compound is administered for a longer treatment period compared to the usual dosing regimen for said active compound.

The quantity (or the expression level) of one or more biomarkers in a sample can be compared, if needed, to a reference quantity (alternatively reference expression level, baseline quantity or baseline expression level) from a reference sample. Said reference level can be obtained from a healthy subject, or from the very same patient to be diagnosed or treated prior to or during said treatment. The width of the joint space of a subject can be compared, if needed, to a reference joint space width (or a baseline joint space width). Said reference width can be obtained from a healthy subject, or from the very same patient to be diagnosed or treated prior to or during said treatment.

The present invention further encompasses an active compound for use in the treatment of a subject having a cartilage disorder, characterized in that the subject has either 1) lower than 350 ng/mmol of CTX-II and/or lower than 4.2 ng/mL of ProC2 and a JSW lower than or equal to 3.5±2SD mm, 2) lower than 350 ng/mmol of CTX-II and/or lower than 4.2 ng/ml of ProC2 and a JSW higher than 3.5±2SD mm, or 3) higher than 350±2SD ng/mmol of CTX-II and/or higher than 4.2±2SD ng/ml of ProC2 and of a JSW lower than 3.5±2SD mm. Although the intermediate sensitive subjects can be treated with the same dosing regimen as the good-sensitive subjects, these subjects may have better benefit with an alternative dosing regimen.

Therefore, the present invention also encompasses an active compound for use according to an alternative dosing regimen (e.g. increased dose of active compound and/or longer treatment period) in the treatment of a subject having a cartilage disorder, characterized in that the subject has either 1) lower than 350 ng/mmol of CTX-II and/or lower than 4.2 ng/ml of ProC2 and a JSW higher than 3.5±2SD mm, or 2) higher than 350±2SD ng/mmol of CTX-II and/or higher than 4.2±2SD ng/ml of ProC2 and of a JSW lower than 3.5±2SD mm. It follows that a subject who does not meet these criteria is preferably excluded from said active compound treatment.

The present invention also relates to an assay to determine sensitivity to an active compound treatment or to determine a treatment regimen with a given active compound, the assay comprising: (a) subjecting a test sample from a human subject, diagnosed as having a cartilage disorder, to at least one assay that determines the quantity of at least one of CTX-II and/or ProC2, (b) determining the quantity of at least one of CTX-II and/or ProC2, and (c) determining from the result of step b), in view of the joint space width measurement, sensitivity or non-sensitivity of said subject to treatment with said active compound. According to said assay, the presence of higher than 350 ng/mmol of CTX-II and/or higher than 4.2 ng/ml of ProC2 together with a JSW higher than 3.5±2SD mm is predictive of non-sensitivity to treatment with an active compound. On the contrary, the presence of lower than 350 ng/mmol of CTX-II and/or lower than 4.2 ng/ml of ProC2 together with a JSW lower than or equal to 3.5±2SD mm is predictive of good-sensitivity. Alternatively, the presence of either 1) lower than 350 ng/mmol of CTX-II and/or lower than 4.2 ng/ml of ProC2 together with a JSW higher than 3.5±2SD mm, or 2) higher than 350±2SD ng/mmol of CTX-II and/or higher than 4.2±2SD ng/ml of ProC2 and of a JSW lower than 3.5±2SD mm, is predictive of intermediate-sensitivity. From the result of said assay, the doctor can easily select only those subjects that are predicted to be sensitives to an active compound treatment, including both intermediate-sensitives and good-sensitives. Before determining the quantity of at least one of the biomarkers, in the above disclosed assays, it is needed to obtain a biomarker (or test) sample of said subject, for instance by blood, serum, synovial fluid or urine collecting.

The present invention is also directed to an assay for selecting a treatment regimen for a human subject with a cartilage disorder, the assay comprising: (a) subjecting a test sample from a human subject, diagnosed as having a cartilage disorder, to at least one assay that determines the quantity of at least one of CTX-II and/or ProC2, (b) determining from step a), in view of the joint space width measurement, the likelihood that said subject is intermediate-sensitive or good-sensitive to an active compound treatment, and (c) determining from the result of step b) the appropriate treatment regimen for said subject. Once the assay is performed, said subject can be selected for and treated with an appropriate dosing regimen comprising an effective amount of an active compound when the subject has lower than 350 ng/mmol of CTX-II and/or lower than 4.2 ng/ml of ProC2 together with a JSW lower than or equal to 3.5±2SD mm based on the recognition that said quantities/width are associated with a good-response to said compound, or when the subject has 1) lower than 350 ng/mmol of CTX-II and/or lower than 4.2 ng/ml of ProC2 together with a JSW higher than 3.5±2SD mm, or 2) higher than 350±2SD ng/mmol of CTX-II and/or higher than 4.2±2SD ng/ml of ProC2 and of a JSW lower than 3.5±2SD mm, based on the recognition that said quantities/width are associated with an intermediate-response to said compound; and excluding the subject from treatment with an active compound when the subject has higher than 350±2SD ng/mmol of CTX-II and/or higher than 4.2±2SD ng/ml of ProC2 together with a JSW higher than 3.5±2SD mm based on the recognition that said quantities are associated with inadequate response to treatment with said compound. Although the intermediate sensitive subjects can be treated with the same dosing regimen as the good-sensitive subjects, these subjects may have better benefit with an alternative dosing regimen. Therefore, alternatively, said intermediate sensitive subjects can be selected for and treated with an alternative dosing regimen (e.g. increased dose of the active compound and/or longer treatment period) with an active compound.

Further discloses is a method for treating a human subject with a cartilage disorder, comprising the steps of: (a) assaying a biological sample of a subject, who is diagnosed as having the cartilage disorder for the quantity of at least one of the biomarkers selected from the group consisting of CTX-II and/or ProC2; (b) measuring a joint space width and (c) administering a treatment regimen comprising a composition comprising an effective amount of an active compound to the subject if the subject has 1) lower than 350±2SD ng/mmol of CTX-II and/or lower than 4.2±2SD ng/ml of ProC2 and if the JSW is lower than or equal to 3.5±2SD mm, 2) lower than 350 ng/mmol of CTX-II and/or lower than 4.2 ng/ml of ProC2 together with a JSW higher than 3.5±2SD mm, or 3) higher than 350±2SD ng/mmol of CTX-II and/or higher than 4.2±2SD ng/mL of ProC2 and of a JSW lower than 3.5±2SD mm. Although the intermediate sensitive subjects can be treated with the same dosing regimen as the good-sensitive subjects, these subjects would have better benefit with an alternative dosing regimen. Therefore, alternatively disclosed is a method for treating a human subject with a cartilage disorder, comprising the steps of: (a) assaying a biological sample of a subject, who is diagnosed as having the cartilage disorder for the quantity of at least one of the biomarkers selected from the group consisting of CTX-II and/or ProC2; (b) measuring a joint space width and (c) administering an alternative treatment regimen (e.g. increased dose of the active compound and/or longer treatment period) comprising a composition comprising an active compound to the subject if the subject has either 1) lower than 350±2SD ng/mmol of CTX-II and/or lower than 4.2±2SD ng/ml of ProC2 and if the JSW is higher than 3.5±2SD mm or 2) higher than 350±2SD ng/mmol of CTX-II and/or higher than 4.2±2SD ng/mL of ProC2 and of a JSW lower than 3.5±2SD mm. In the context of the present invention as a whole, CTX-II and/or ProC2 have been shown to be useful predictive biomarkers of the placebo response and of the response of a subject to an active compound for treating a cartilage disorder. As such they are considered as predictive biomarkers. Other metabolic biomarkers could be alternatively used such as C2M, ARGS or AGNx1.

In the context of the present invention as a whole, the preferred cartilage disorder is selected from the group consisting of osteoarthritis, cartilage injury, fractures affecting joint cartilage or surgical procedures with impact on joint cartilage, such as microfracture.

In the context of the present invention as a whole, e.g. in the context of any one of the methods, uses, assays or kits according to the present invention, the preferred active compounds can be selected from an FGF-18 compound (including truncated FGF-18 compound such as sprifermin), BMP-2, BMP-7, GDF-5, FGFβ, FGF-9, SOX-9 enhancers, TGFβ, Wnt inhibitors, anti-MMP13 inhibitors, anti-ADAMTS4 or 5 inhibitors, calcitonin and any variants or fusion protein thereof.

As examples of dosing schedule, if the active compound according to the present invention as a whole is an FGF-18 compound, said FGF-18 compound is to be usually administered intraarticularly to a subject (preferably a good-sensitive subject) at a dose of 100 mcg per injection, once weekly for 3 weeks per treatment cycle. A proposed dosing regimen for these subjects predicted to be high-sensitives is intraarticular administration of the FGF-18 compound at a dose of 30 mcg per injection, once weekly for 3 weeks per treatment cycle. It is to be understood that although at that time, the preferred dose is 100 mcg per injection, possibly reduced to 30 mcg per injection for super-sensitives, the present invention is not limited to said dosages. Therefore, FGF-18 compound can be administered intraarticularly at a dose comprised between 50 and 300 mcg per injection, preferably between 60 and 250 mcg or even preferably between 100 and 200 mcg. For super-sensitive subjects, said dose could be reduced, to or to about ½ or to or to about ⅓ for instance. For examples, should the normal dose be 50 mcg per injection, the reduced dose could be comprised between 16 and 25 mcg per injection. FGF-18 compound is to be usually administered for at least one cycle of treatment. Preferably, said cycle is repeated at least once, for instance 6 months (or about 26 weeks) after the start of the first treatment cycle. Up to four treatment cycles within 2 years have shown promising results (see FIG. 1). Obviously, should the subject be predicted to be intermediate-sensitive to an active compound, an alternative dosing regimen could consist of additional treatment cycles.

As another example of dosing schedule, if the active compound according to the present invention as a whole is a calcitonin compound, said calcitonin compound is to be usually administered orally at a twice daily dose of 0.8 mg for up to 24 months or longer if needed or any typical dosing regimen administered for said compound. Should it be needed, the oral dose and the length of the treatment can be adapted to the response or likelihood of response of the subject to said treatment in order an intermediate responder benefits from said calcitonin treatment.

In a yet other example of dosing schedule, if the active compound according to the present invention as a whole is a BMP-7 compound, said BMP-7 compound is to be usually administered intraarticularly at a dose of about 0.03 mcg/ml to 0.3 mcg/ml such as 0.3, 0.1 or 0.3 mcg/mL per injection, possibly repeated. or any typical dosing regimen administered for said compound. Should it be needed, the oral dose and the length of the treatment can be adapted to the response or likelihood of response of the subject to said treatment.

In the context of the present invention as a whole, the assays or other determination of the quantity of at least one of the biomarkers of the invention can be performed before treatment or during treatment. Indeed, also during treatment the dosing regimen may have to be adapted to the new markers situation. In the context of the invention as a whole, for the patients being in the range of 350±2SD ng/mmol of CTX-II or of 4.2±2SD ng/mL of ProC2, it is advisable to complete the diagnostic or the biomarker testing with another metabolic biomarker. For instance, should the level of CTX-II be in the range of 350±2SD ng/mmol, then the level(s) of ProC2 could be considered. In the rare case where the patient will present ranges of 350±2SD ng/mmol of CTX-II and of 4.2±2SD ng/ml of ProC2, then it will be advisable to complete the diagnostic or the biomarker testing with another kind of biomarker such as an inflammatory biomarker or SNP biomarkers such as those disclosed in WO2014023703.

In the context of the invention as a whole, the width of a joint space is preferably determined by X-ray radiography or MRI technics. Obviously, the skilled person can use alternative technics should he prefer. In another embodiment of the invention, also provided are systems (and computer readable media for causing computer systems) for obtaining data. Said data can be used notably for assessing suitability for a clinical trial or suitable of a treatment with an active compound in a subject or monitoring the treatment efficacy of an active compound for a given subject or simply monitor disease progression. Said systems can be used during clinical trials, when a treatment with an active compound for treating a cartilage disorder has to be envisaged or when a treatment with said compound is already ongoing.

Therefore, in an embodiment of the present invention is included a computer system for obtaining data from at least one test sample obtained from at least one subject with a cartilage disorder together with the data related to the JSW for said subject, the system comprising: (a) at least one determination module configured to receive the data related to the JSW from one patient together with at least one test sample from said subject and perform at least one analysis on said at least one test sample to determine the quantity of at least one of the biomarkers according to the invention; (b) at least one storage device configured to store data output from said determination module; and (c) at least one display module for displaying a content based in part on the data output from said determination module, wherein the content comprises a signal indicative of the presence of at least one of these conditions, and optionally the absence of any one of these conditions.

The computer readable medium can have computer readable instructions recorded thereon to define software modules for implementing a method on a computer. In such a case, said computer readable storage medium may comprise:

(a) instructions for comparing the data stored on a storage device with reference data to provide a comparison result, wherein the comparison is based on the quantity of at least one of the biomarkers and on the width of a joint space according to the invention; and (b) instructions for displaying a content based in part on the data output from said determination module, wherein the content comprises a signal indicative of the presence of at least one of the conditions, and optionally the absence of one or more of the conditions.

The computer readable storage media can be any available tangible media that can be accessed by a computer. Computer readable storage media includes volatile and 21 on-volatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J #, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein.

The information determined in the determination module can be read by the storage device. The storage device is adapted or configured for having recorded thereon expression level or protein level information. Such information may be provided in digital form that can be transmitted and read electronically, e.g., via the Internet, on diskette, via USB (universal serial bus) or via any other suitable mode of communication. It is to be understood that in the context of the present invention as a whole, e.g. of any one of the methods, uses, assays, computer system or kits according to the present invention, before determining the quantity of at least one of the biomarkers of the invention (e.g. CTX-II and/or ProC2), it is needed to obtain a sample (or biological sample or a test sample) of one subject, for instance by blood, serum, synovial fluid or urine collecting. It can also be obtained, without any limitation, from a cell, tissue, cartilage or synovial fluid.

An individual afflicted with a cartilage disorder and to be tested, tested and/or treated according to any of the methods, uses, assays, kits and other computer systems described herein is a human subject that is a candidate for treatment with an active compound for treating said cartilage disorder. In a preferred embodiment, the individual has been diagnosed with cartilage disorder, or exhibits a symptom of cartilage disorder.

In a further embodiment, the present invention encompasses a kit comprising means for performing the methods described above and instructions for use. Preferably, the kit comprises means for detecting the presence of at least one of the biomarkers according to the invention (e.g. CTX-II and/or ProC2) and for quantifying them. The kit may comprise means for detecting the presence of at least two of the biomarkers according to the invention and for quantifying them. The results obtained from the kit will have to be combined with the result of measurement if JSW before reaching any conclusion The methods and kits according to the present invention are useful in clinical diagnostic applications. However, as used herein, the term "diagnostic" is not limited to clinical or medical uses, and the diagnostic methods and kits of the invention claimed herein are also useful in any research application, and during clinical trials, for which it is desirable to test a subject for the presence or absence of any marker described herein.

In the context of the invention, the presence of at least one of the biomarkers according to the invention (e.g. CTX-II and/or ProC2) and their quantitation may be detected by any technique known per se to the skilled artisan, including ELISA.

Other embodiments of the invention within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the examples.

DESCRIPTION OF THE FIGURES

In FIGS. 6A-D, each group of treated patients (groups 2 to 5) from the FORWARD study were compared to the placebo group (group 1) (comparison based on the difference to the placebo). Data are group medians.

DESCRIPTION OF THE SEQUENCES

Figure 1:
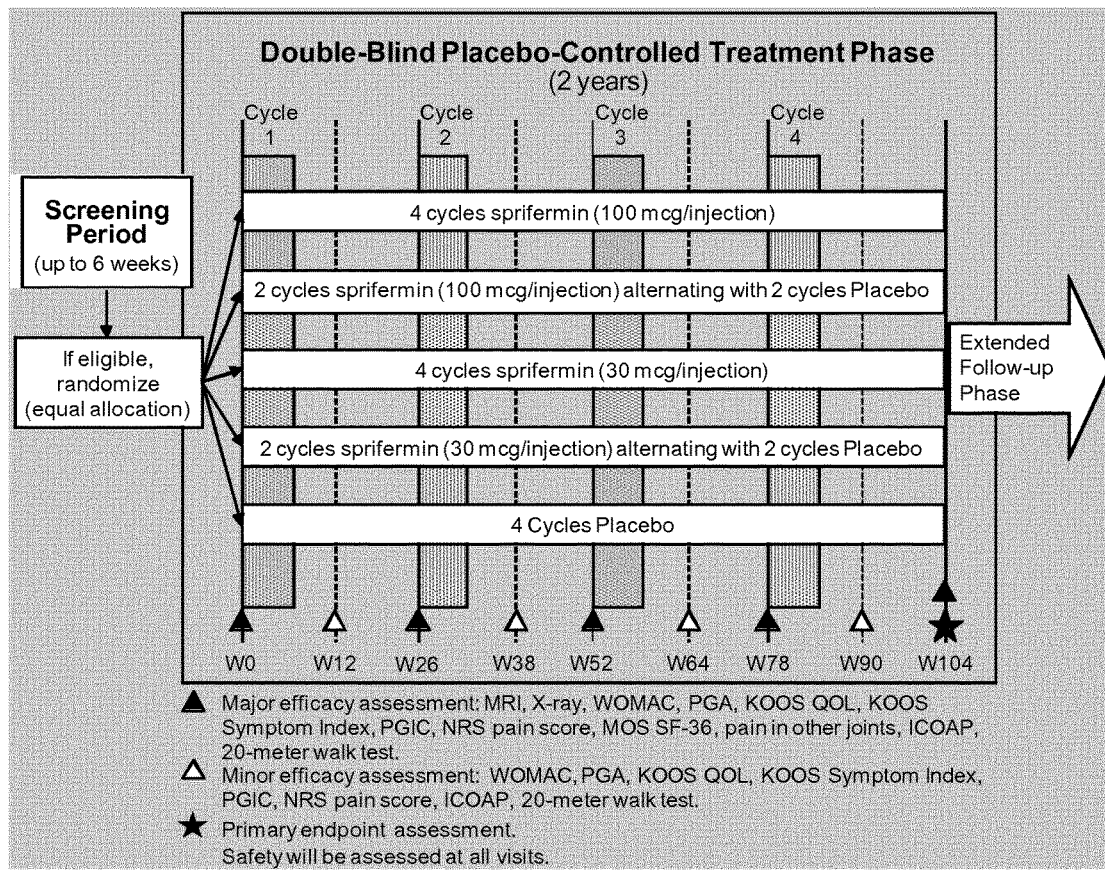
FIG. 1: Scheme of the dosing regimens used for FGF-18 compound in the FORWARD study.
Figure 2:
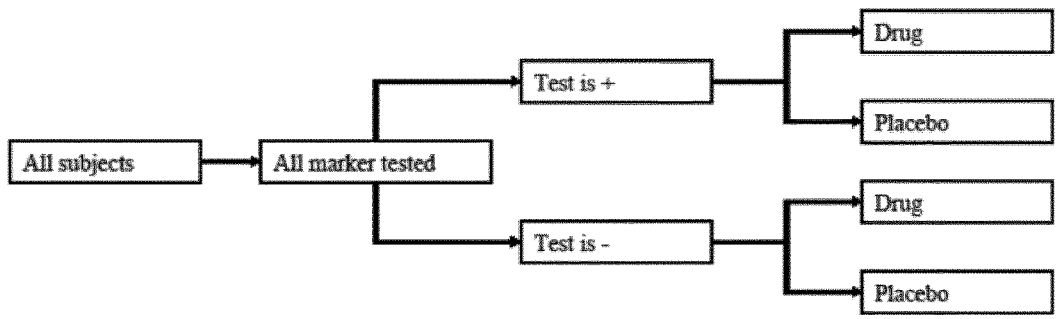
FIG. 2: Proposed enrichment strategy from FDA draft guidance "Enrichment Strategies for Clinical Trials to Support Approval of Human Drugs and Biological Products" (FDA, 2012).

SEQ ID NO. 1: Amino acid sequence of the biomarker CTX-II.
SEQ ID NO. 2: Amino acid sequence of the biomarker PROC2.
SEQ ID NO. 3: Amino acid sequence of the native human FGF-18.
SEQ ID NO. 4: Amino acid sequence of the recombinant truncated FGF-18 (trFGF-18).
SEQ ID NO. 5: Amino acid sequence of the salmon calcitonin.
SEQ ID NO. 6: Amino acid sequence of the human BMP-2
SEQ ID NO. 7: Amino acid sequence of the human BMP-7
SEQ ID NO. 8: Amino acid sequence of the human GDF-5.
SEQ ID NO. 9: Amino acid sequence of the human FGFβ.
SEQ ID NO. 10: Amino acid sequence of the human FGF-9.

EXAMPLES

Statistical Methods

The treatment effect on the primary endpoint was assessed through dose-ranging using a repeated measurement analysis of variance (ANOVA, using PROC MIXED in SAS) on absolute change from Baseline, including the baseline value, the treatment group, the time, and the country as factors and treatment-by-time point as interaction. The primary efficacy analysis consisted of testing the linear dose relationship and the overall treatment effect at 2 years. The significance level was set at 5% 2-sided for both tests. Pairwise comparisons (sprifermin versus placebo, and between sprifermin dose and regimen groups) were performed within the context of this modelling framework. For each pairwise comparison, the difference between treatments and the corresponding 95% confidence interval (CI) and p-value are presented. The same ANOVA model used for the primary endpoint was used to assess the treatment effect on continuous secondary endpoints such as MRI endpoints, WOMAC endpoints (total, pain, function, and stiffness scores), and X-ray endpoints at each time point and over time. Logistic regression was used to assess the treatment effect on the binary efficacy endpoints such as the OMERACT-OARSI responder rate. Point estimates for each pairwise comparison and corresponding 95% CIs and p-values are provided.

Pain and Function Assessments

The WOMAC is a validated instrument used to assess symptom modification in clinical OA studies. This clinical score was developed in 1981 and is regarded as a valid instrument by both clinical researchers and regulatory authorities. The WOMAC is widely used in clinical studies in hip and knee OA and has been extensively validated.

Subjects had to answer all of the 24 questions themselves (i.e. 5 for pain, 2 for stiffness and 17 for physical function assessment), using either the 11-box NRS assessment (with categories of 0 to 10) with reference to the past 48 hours for example 1 or 100 mm VAS (visual analogue scales; giving each question a score from 0 to 100) with reference to the past 24 hours for example 2. Different forms of the questionnaire exist for the right and the left knees: in order to reduce confounding of WOMAC responses by symptoms in the contralateral knee, subjects used the WOMAC questionnaire specific to the target knee.

For administration of the questionnaire, instructions for the WOMAC 3.1 Index were followed for both examples 1 and 2.

Other instruments for assessment of pain and function are the KOOS (Knee injury and Osteoarthritis Outcome Score, Collins et al. 2016).

X-Ray Assessment of JSW

Change in JSW as measured by X-ray is a recognized endpoint accepted by the European Medicines Agency and the United States Food and Drug Administration for use in efficacy studies in OA. The JSW was measured using standardized technique. X-ray was also used to assess KL grade in example 2.

gMRI Assessment

The primary endpoint for the DBPC treatment phase was the change from Baseline in cartilage thickness in the total femorotibial joint as evaluated by qMRI at 2 years in the mITT. Cartilage thickness of the total femorotibial joint were calculated in 2 ways:

1. Average Cartilage Thickness (Total Volume divided by Total Surface Area),
2. Total Cartilage Thickness (sum of cartilage thickness in medial and lateral compartment).

The treatment effect on the primary endpoint was assessed through dose-ranging using a repeated measurement analysis of variance (ANOVA) on absolute change from Baseline, including the treatment group, the time point, and the (pooled) country as fixed factors and the baseline value as covariate and treatment by time point as interaction. Repeated measures over time were accounted for using an "unstructured" covariance pattern.

Pairwise comparisons of absolute change from Baseline in cartilage thickness (treatment with compound groups versus placebo) were performed within the context of the modelling framework described above. For each pairwise comparison, the difference between treatments and the corresponding 95% confidence interval (CI) and p-value are presented. P-values (corresponding to Type 3 tests of fixed effects) are reported for all covariates in the original "Overall" model for all time points combined (i.e., baseline value, treatment, time point, treatment-by-time point interaction, country) and for all time points. Estimated coefficients, p-values, and 95% CIs are presented overall and at each time point for (i) the dose relationship (linear trend) and (ii) each pairwise comparison between dose level and placebo.

In order to assess the robustness of the primary results, the tests for linear dose-relationship and for the overall treatment effect were repeated using the PP Analysis Set. For the mITT Analysis Set, a non-parametric analysis was conducted for the ordered data of cartilage thickness in the total femorotibial joint as an alternative method for the primary analysis. Data were ordered by the magnitude of absolute change-from-Baseline over 2 years during DBPC treatment phase using rank transformation.

Biomarkers Measurement

Serological and urine biochemical markers of bone and joint tissue turnover as well as synovial inflammation were evaluated. Potential biomarkers of cartilage metabolism included, but were not limited to: neo-epitope of collagen type II propeptide (proC2) and C-telopeptide cross-linking of type II collagen (CTX-II). Blood and urine samples for systemic biomarker assessment were collected at the following time points: week 0 (before first injection of sprifermin), week 26, week 54, week 80 and week 104. For time points where injections were also administered, samples were collected before injection. Synovial fluid samples were collected at the time points. These samples were taken just before injection, as part of the i.art. injection procedure and using the same needle that the one used for the injection. For urine collection, second morning void samples were obtained.

The following assessment were made as exploratory endpoints:
  Change from Baseline in serum and urine biomarkers associated with administration of the compound.
  Baseline protein markers associated with response to treatment or disease progression (response assessed by MRI and/or questionnaire).

Example 1. Placebo Response and of the Clinical Efficacy in Subjects Treated with an FGF-18 Compound The FGF-18 compound used as a treatment in the present examples is sprifermin (as defined in the section "definitions"). Two strengths of sprifermin were supplied for the study: 30 µg and 100 µg. Sprifermin was supplied as a white, sterile, freeze-dried powder in 3-mL glass vials. Each vial contained either 31.5 µg or 105 µg of sprifermin active substance; these quantities included a 5% overage, permitting extraction of respectively 30 µg or 100 µg of sprifermin active substance following reconstitution with 0.9% w/v Sodium Chloride Injection (referred to herein as "saline solution"). Excipients of the formulation were sodium phosphate buffer (pH 7.2), sodium hydroxide, O-phosphoric acid, sucrose, and poloxamer 188. For all treatment groups, the volume administered was 2 mL.

The present study was based on the FORWARD study (see study EMR700692-006) where five groups of patients were studied:
  Group 1 (4 cycles placebo; hereafter referred to as placebo or PBO): 108 subjects.
  Group 2 (2 cycles sprifermin 30 µg/injection alternating with 2 cycles placebo; hereafter referred to as sprifermin/placebo 30 µg): 110 subjects.
  Group 3 (4 cycles sprifermin 30 µg/injection; hereafter referred to as sprifermin 30 µg): 111 subjects.
  Group 4 (2 cycles sprifermin 100 µg/injection alternating with 2 cycles of placebo; hereafter referred to as sprifermin/placebo 100 µg): 110 subjects.
  Group 5 (4 cycles sprifermin 100 µg/injection; hereafter referred to as sprifermin 100 µg): 110 subjects.

According to the FORWARD study, the patients received 4 cycles of treatment (each consisting of 3 once-weekly intra articular injections over 3 consecutive weeks) at intervals of 6 months (see FIG. 1). All injections were intraarticular (done intraarticularly).

The primary efficacy endpoint was the change from Baseline in cartilage thickness in the total femorotibial joint as evaluated by MRI at 2 years. Exploratory endpoints included Baseline protein markers associated with response to treatment or disease progression (response assessed by MRI and/or questionnaire).

The study enrolled adult subjects of either sex with primary femorotibial OA according to American College of Rheumatology (ACR) clinical and radiographic criteria who had Kellgren-Lawrence grades (KLG) of 2 or 3 and a minimum joint space width (JSW) of ≥2.5 mm in the medial compartment. Subjects must have had pain in the target knee on most days and/or require symptomatic treatment of knee pain with paracetamol (acetaminophen), systemic non-steroidal anti-inflammatory drugs (NSAIDs) including COX inhibitors (COXibs), or tramadol on most days of the previous month, and must have had both: 1) A history of pain due to OA in the target knee for at least 6 months, and 2) Pain score for the target knee of 4 to 9 points in response to Question 1 of the Western Ontario and McMaster Universities Osteoarthritis Index (WOMAC) pain index ("how much pain have you had [in the target knee, over the past 48 hours] when walking on a flat surface?") at screening and Baseline, after washout of at least 5 half-lives of analgesic medication(s): acetaminophen, topical or oral systemic NSAIDS, COXibs, opioids, and/or tramadol. Women of childbearing potential must have used a form of contraception with a failure rate of less than 1% per year throughout the study.

Main exclusion criteria included malalignment of >5 degrees in the femorotibial axis of the target knee, clinical signs of inflammation (i.e. redness) in the target knee, i.art. administration of corticosteroids or hyaluronic acid into either knee within 6 months before screening, any plan for knee surgery (affecting either the target or the contralateral knee) within the next 2 years, concomitant conditions or treatments deemed to be incompatible with study participation, contraindications to MRI scanning (including inability to fit in the scanner or knee coil), pregnancy or breastfeeding, participation in another clinical study within the past 30 days, and legal incapacity or limited legal capacity.

Written informed consent must have been obtained prior to any study-related activity.

Figure 3:
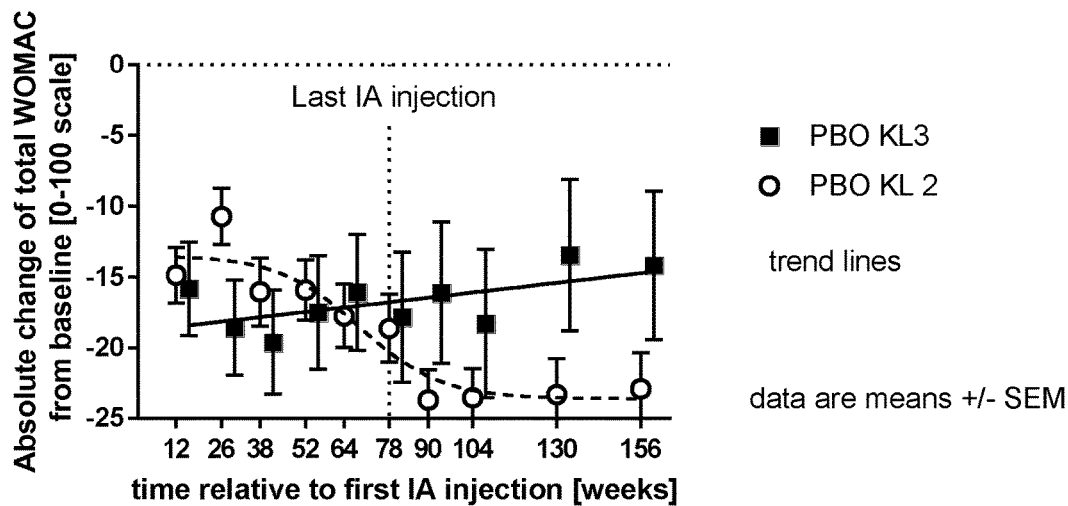
FIG. 3: Placebo responses in KL2 and KL3 patients (i.e. placebo effect as a function of the JSW) underlined via total WOMAC score. A) Total WOMAC change from baseline in KL2 and KL3 groups as a function of the elapsed time after first IA injection group means as a function of time elapsed (data are means+/−SD). B) Total WOMAC score in KL2 and KL3 groups as a function of the elapsed time after first IA injection group means as a function of time elapsed (data are medians).
Figure 3:
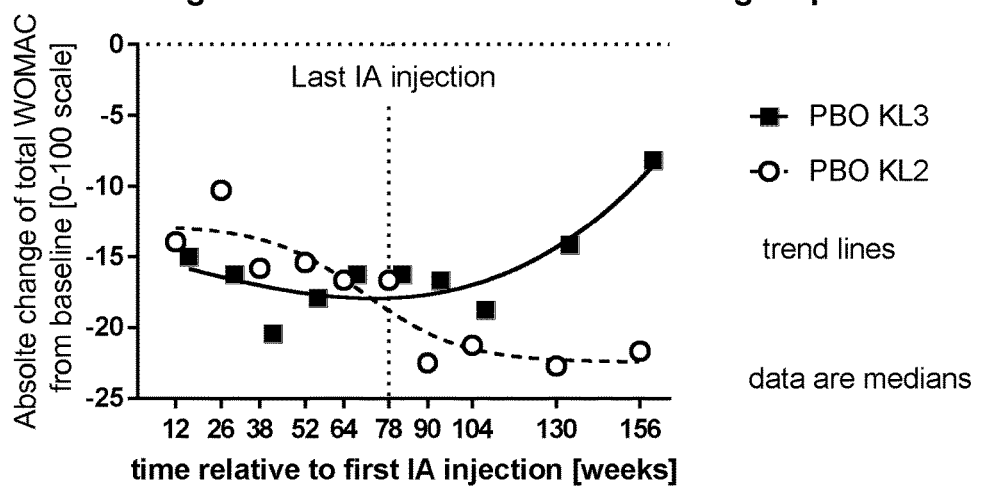

Placebo effect based on JSW alone: As shown in FIG. 3 (both A and B), the placebo effect in KL2 patients (having a JSW >3.5 mm) versus KL3 patients (having a JSW≤3.5 mm) is very important. As self-evident, it plays an important role on the total WOMAC score, where the simple injection of a placebo (PBO) (i.e. a salt) is enough to reduce drastically over a very long time the WOMAC score in KL2 patients, whereas said WOMAC score increase continuously in KL3 patients, despite the injection.

Figure 4:
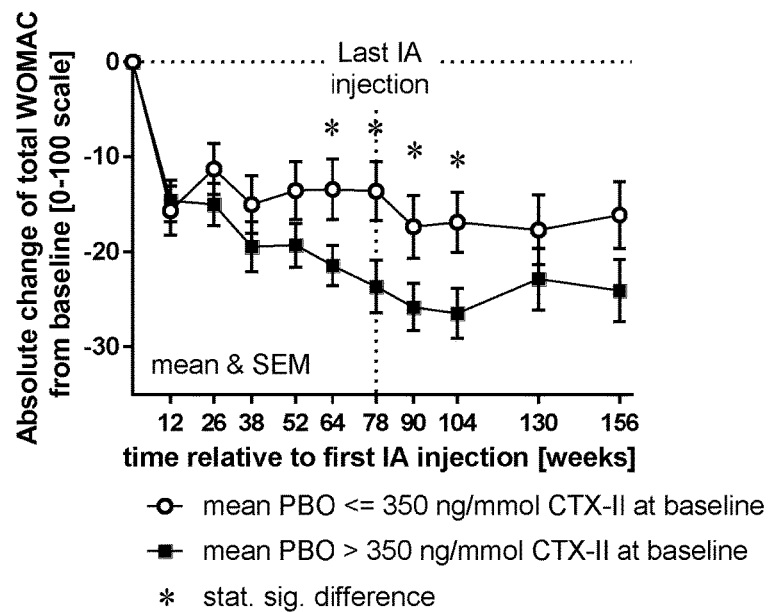
FIG. 4: Placebo responses as a function of the biomarkers level underlined via total WOMAC score. A) Total WOMAC change in group as a function of elapsed time, based on the CTX-II level (group 1: ≤350 ng/mmol and group 2: >350 ng/mmol) (data are means+/−SD). B) Total WOMAC change in group as a function of elapsed time, based on the ProC2 level (group 1: ≤4.2 ng/mmol and group 2: >4.2 ng/mmol) (data are means+/−SD).
Figure 4:
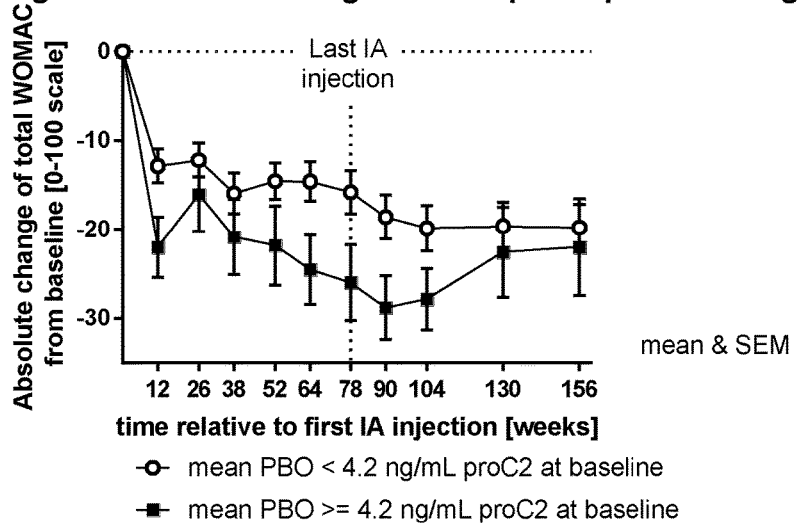

Placebo effect based on CTX-II or ProC2 levels: FIG. 4 underlines that the patients having a high metabolic biomarker level such as CTX-II above 350 ng/mmol (FIG. 4A) or ProC2 above 4.2 ng/ml (FIG. 4B) present a higher placebo effect to injection of a placebo.

Figure 5:
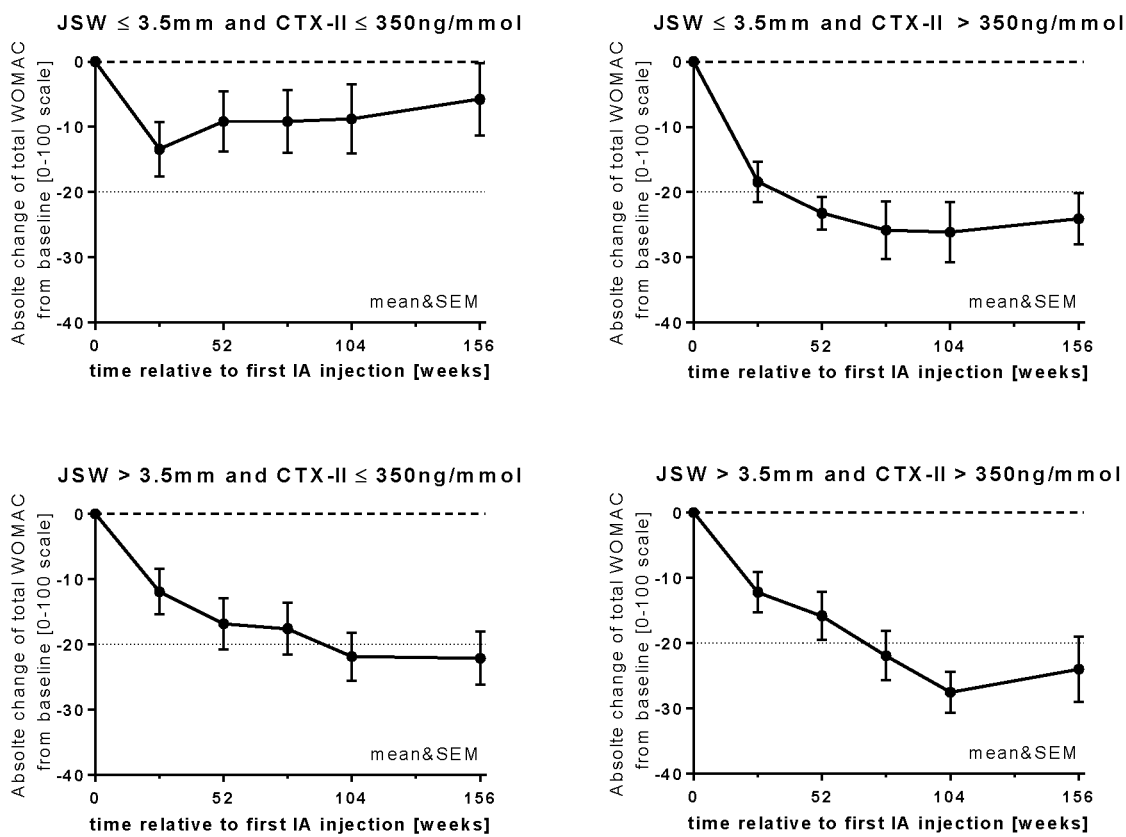
FIG. 5: Placebo responses combining both JSW measurments) and CTX-II level underlined via total WOMAC score in group means as a function of time elapsed (months). The data is retrieved from the placebo arm of the FOR-WARD study.

Placebo effect based on a combination JSW+CTX-II level: As shown in FIG. 5, different distribution of CTX-II levels at baseline influence outcome measures like MRI and WOMAC. In view of the results, thin cartilage (JSW≤3.5 mm) and low level of metabolic biomarkers (e.g. CTX-II below or equal to 350 ng/mmol) seems the right study population for a clinical trial to mitigate elevated placebo responses.

After treatment with FGF18: As evident from FIGS. 6A and 6B, once the placebo effect is taken into consideration, the shape of response in term of total WOMAC score, for both KL2 patients and KL3 patients treated with various doses of sprifermin, change drastically. The same is true when the CTX-2 level are taken into consideration.

Figure 6:
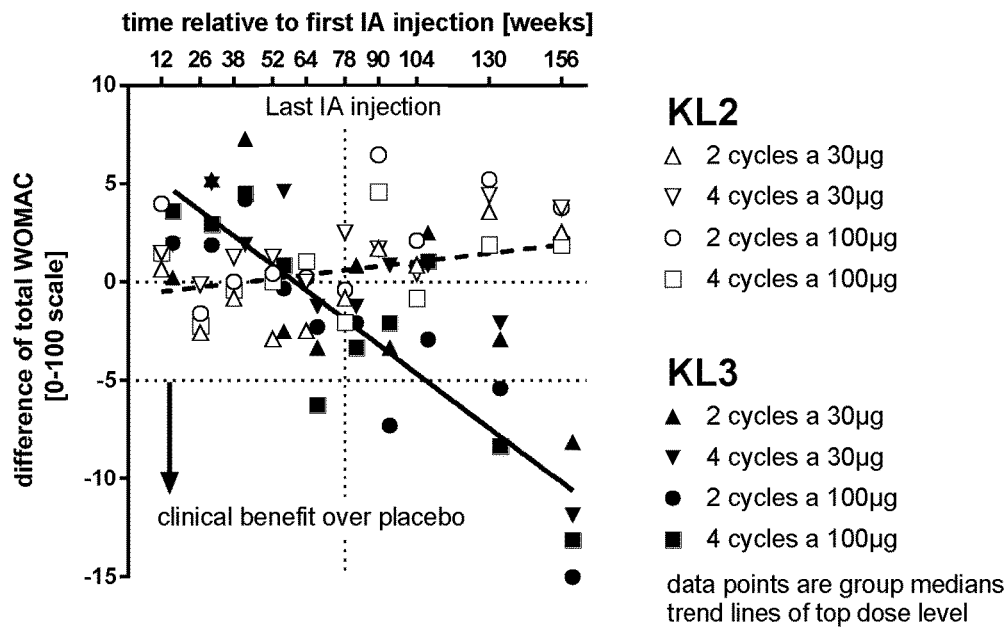
FIG. 6: A) Difference of active arms to the placebo arm as a function of the KL grade of the patients and as a function of elapsed time after first IA injection, demonstrated with Total WOMAC score. B) Difference of active arms to the placebo arm as a function of the CTX-II level of the patients and as a function of elapsed time after first IA injection, demonstrated with Total WOMAC score. C) Difference of active arms to the placebo arm as a function of the KL grade of the patients and as a function of elapsed time after first IA injection, demonstrated with cartilage thickness level. B) Difference of active arms to the placebo arm as a function of the CTX-II level of the patients and as a function of elapsed time after first IA injection, demonstrated with cartilage thickness level.
Figure 6:
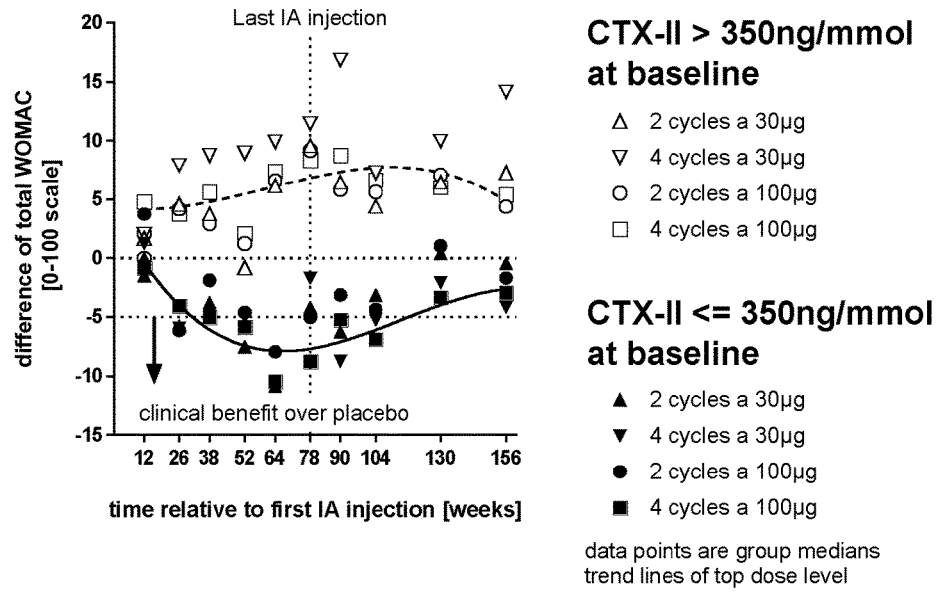
Figure 6:
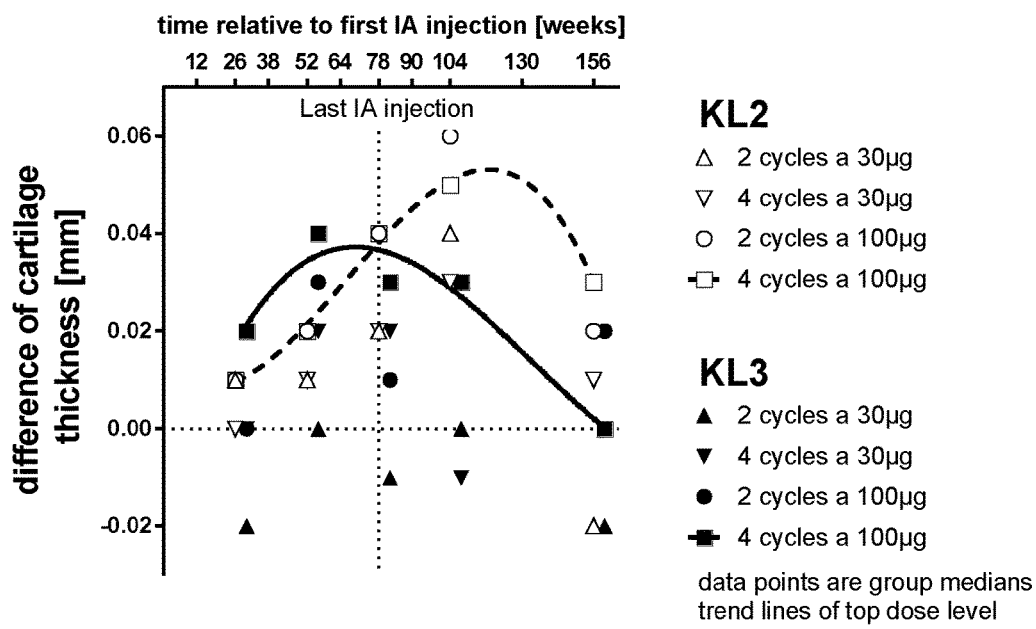
Figure 6:
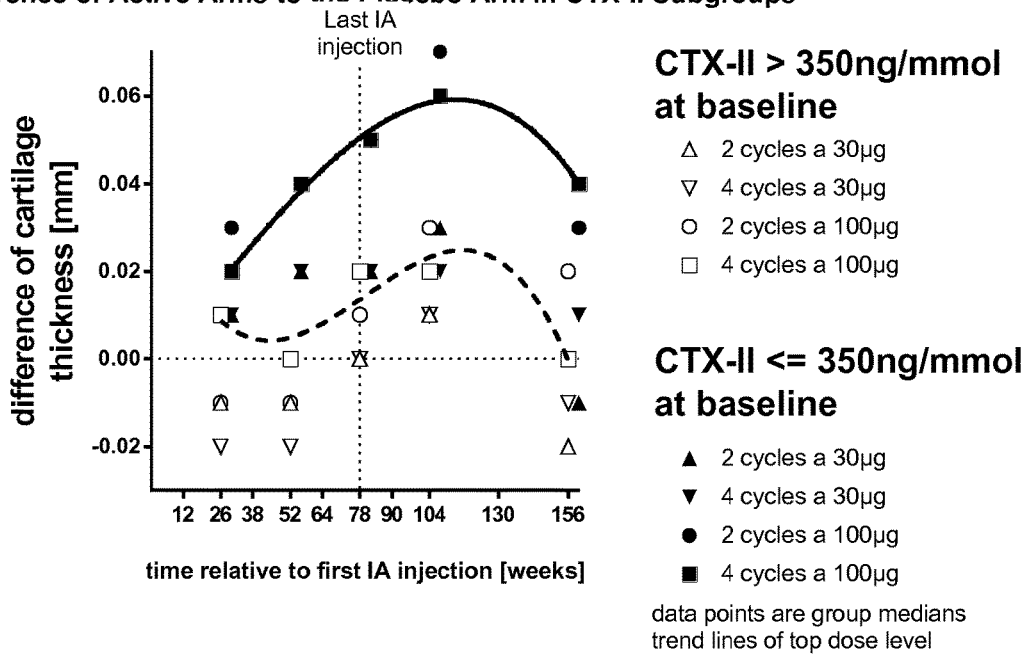

As evident from FIGS. 6C and 6D, once the placebo effect is taken into consideration, the shape of response in term of cartilage thickness also change deeply, for both KL2 patients and KL3 patients treated with various doses of sprifermin. The same is true when the CTX-2 level are taken into consideration.

From this example it is clear that stratification can de-risk clinical trial which are otherwise biased by the placebo effect of some subgroups of patients.

Example 2. Placebo Response in Subjects Treated with Placebo from a Study with Compound X The study was double blinded, randomized, placebo-controlled and multi-centre clinical trial for the assessment of compound X. There were about 600 patients enrolled in the placebo arm of this study. Patients aged 50-80 years with painful OA of at least one knee, but who were otherwise in good general health were recruited. Compound X being an oral drug, the placebo was supplied in identical packaging. To be included, patients had to meet the ACR criteria for diagnosis of OA. Both knees were assessed during the study, but a target knee was identified prior to randomization for assessment of the primary efficacy endpoint. The target knee had to be painful on most days of the prior month. In addition, the patient had to fulfil at least one of the following criteria: age over 50 years, experience morning stiffness lasting less than 30 min, or knee crepitus. The target knee had to have a JSW ≥2.0 mm at the medial tibio-femoral joint as measured on X-ray and have a KL score of 2 or 3. On WOMAC, patients were to score ≥150 mm for pain and/or ≥510 mm for function. If both knees fulfilled the criteria, the target knee was defined as the knee that meets KL score of 2. If both knees had KL scores of 2 the knee with the highest pain VAS was selected (as long as it was below 80 mm).

Exclusion criteria included diseases (apart from OA) and medications that affected bone or cartilage metabolism. Pain relief medication was allowed, provided it was taken at least 30 min after the study drug. Intra-articular injection of corticosteroids or hyaluronic acid in the target knee was prohibited during the study and 3 months prior to randomization.

Randomization was stratified by centre and it was ensured that treatment assignment was unbiased and concealed from patients and investigator staff. The trial was conducted in accordance with the Declaration of Helsinki. The protocol was approved by independent ethics committees or institutional review boards (IEC/IRB). All subjects or legal representatives gave their informed consent to take part.

Figure 7:
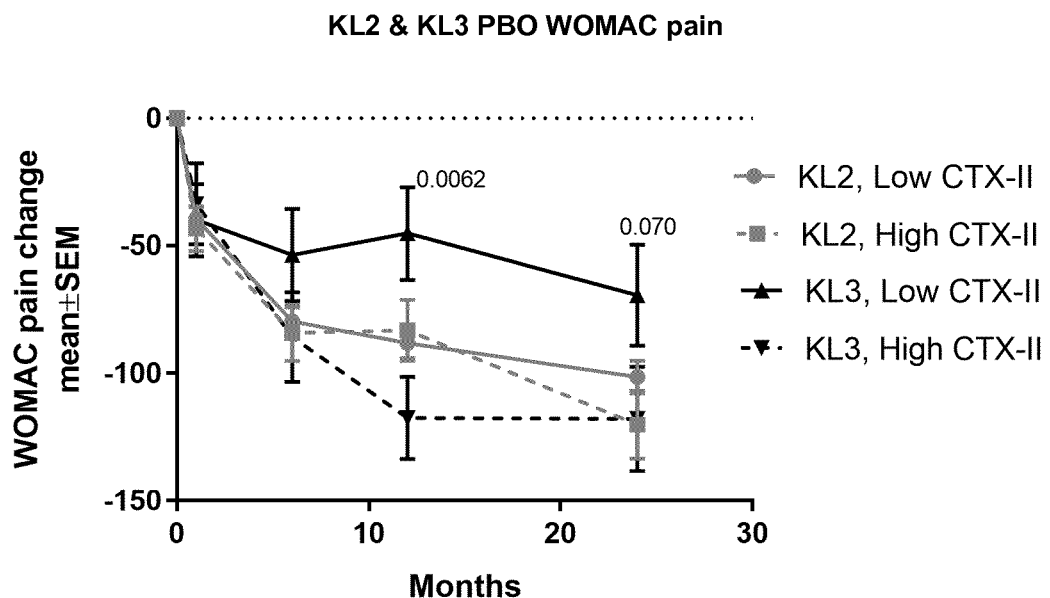
FIG. 7: Placebo responses combining both JSW (expressed as KL2 and KL3) and CTX-II level underlined via change in WOMAC pain score in group mean (SEM) as a function of time elapsed (months). The number of patients in each subgroup are as follows, n=380 (KL2 with low CTX-II), n=90 (KL2 with high CTX-II), n=40 (KL3 with low CTX-II) and n=20 (KL3 with high CTX-II).

Placebo effect based on a combination KL+CTX-II level: As shown in FIG. 7, different distribution of CTX-II levels in subgroups of KL2 and KL3s at baseline influence outcome measures like WOMAC pain. In view of the results, thin cartilage (JSW≤3.5 mm) and low level of metabolic biomarkers (e.g. CTX-II below or equal to 350 ng/mmol) seems the right study population for a clinical trial to mitigate elevated placebo responses.

OVERALL CONCLUSION

Figure 8:
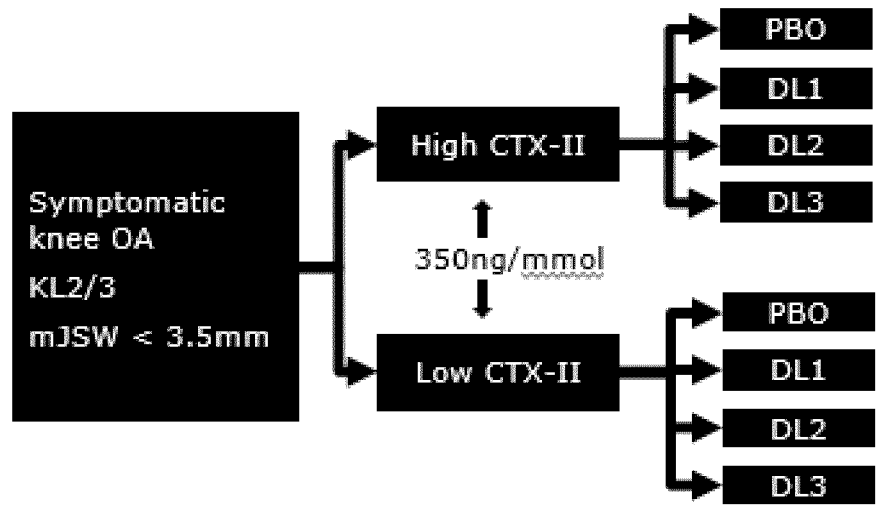
FIG. 8: Proposed enrichment strategy for any clinical trials in Osteoarthritis, based on the FDA draft guidance of 2012.

The examples clearly underlined that KL3 enriched and CTX-II balanced design would enable detection of symptomatic benefit up to at least year 3 (see FIG. 8). Therefore, thin cartilage (below or equal to 3.5±2SD mm) and low CTX-II (below or equal to 350±2SD ng/mmol) seems the best study population for a clinical trial to mitigate elevated placebo responses. Of notes, it is obviously possible to use Allcomer data, i.e.no loss of patients: it is just a matter of stratification, of management of the patients. Similarly, based on the results of the example section, ProC2 level could be used instead of CTX-II level. In such a case, thin cartilage and low ProC2 (below or equal to 4.2±2SD ng/ml) would be an equally appropriate study population for a clinical trial to mitigate elevated placebo responses.

Thanks to these findings, demonstrated for two very different clinical trial involving two very different active compounds, administered via different routes (one injected intraarticularly and the other administered orally), and to this proposed stratification, it is possible to decrease placebo responses, avoid misbalance between treatment groups and de-risk clinical trial for any drugs targeting OA due to possibility to select the right patient population with structural and symptomatic benefit.

REFERENCES

1) WO2008/023063
2) WO2004/032849
3) WO2014/023703
4) www.cartilage.org/_files/contentmanagement/ICRS_evaluation.pdf
5) Lotz, 2010, Arthritis research therapy, 12:211
6) Ellsworth et al., 2002, Osteoarthritis and Cartilage, 10:308-320
7) Shimoaka et al., 2002, J. Bio. Chem. 277 (9): 7493-7500
8) Gigout et al., 2017, Osteoarthritis and Cartilage, published online the 18 Aug. 2018 (doi.org/10.1016/j.joca.2017.08.004)
9) Lohmander et al., 2014, Arthritis Rheumatol., July; 66 (7): 1820-31
10) Dahlberg et al., 2016, Clin Exp Rheumatol., May-June; 34 (3): 445-50
11) Deng et al. 2018, Osteoarthritis and Cartilage, in press: 1-9
12) Parrish et al., 2017, Osteoarthritis Cartilage., April; 25 (4): 554-560
13) Ameye and Young 2006. Curr Opin Rheumatol 18:537-547.
14) Zhou et al., 2016, Osteoarthritis Cartilage., December; 24 (12): 2181-2192
15) Wang et al. 2014. Birth defects Res C embryo today 102:37-51
16) Karsdal et al., 2016, Osteoarthritis and Cartilage, 24 (12): 2013-2021

17) Duclos et al., 2010, Osteoarthritis Cartilage. 2010 November; 18 (11): 1467-76.
18) Gudmann et al., 2016, Arthritis Res Ther., 18 (1): 141.
19) Munk et al., 2016, Rheumatol Int. 36 (4): 541-9.
20) Gudmann et al., 2014, Int J Mol Sci., 15 (10): 18789-18803.
21) Valdes et al., 2014, Osteoarthritis Cartilage., May; 22 (5): 683-9
22) Struglics et al., 2011, Osteoarthritis Cartilage., August; 19 (8): 1047-57
23) Struglics et al., 2015, Arthritis Rheumatol., July; 67 (7): 1816-25
24) The Merck Manual, 17$^{th}$ edition, page 449
25) Bellamy et al., 1988, J. Rheumatology, 15:1833-1840
26) Wolfe, 1999, Rheumatology, 38:355-361
27) Bay-Jensen et al., 2016, Osteoarthritis Cartilage. 24 (1): 9-20
28) Collins et al. 2016. Osteoarthritis Cartilage 24:1317

ABBREVIATIONS

BMI=Body mass index; CI=confidence interval, DBPC=double-blind placebo-controlled
CTX-II=C-telopeptide cross-linking of type II collagen, DBPC=Double-Blind Placebo Controlled
ICOAP=Measure of Intermittent and Constant Osteoarthritis Pain
ITT=intention-to-treat; JSW=Joint Space Width
KOOS Symptom Index=Knee Injury and Osteoarthritis Outcome Score symptom index subscale
KOOS QOL=Knee Injury and Osteoarthritis Outcome Score quality of life subscale
LOCF=last observation carried forward,
LFTC=lateral femoro-tibial compartment
MFTC=medial femoro-tibial compartment
mITT=modified intention-to-treat
MOS SF-36=Medical Outcomes Study Short Form-36 General Health Survey
MRI=magnetic resonance imaging
NRS pain score=numerical rating scale pain score
OA=Osteoarthritis
PGA=Patient's Global Assessment
PGIC=Patient's Global Impression of Change
PROC2=neo-epitope of collagen type II propeptide
WOMAC=Western Ontario and McMaster Universities Osteoarthritis Index; W=Week

The invention claimed is:

1. A method for treating a subject with an FGF-18 compound having a cartilage disorder characterized by articular cartilage injury or loss of articular cartilage, comprising the following steps:
   a) determining, from a sample from said subject, the quantity of neo-epitope of Collagen type II (ProC2), and a measurement of the joint space width (JSW) in at least one knee of said subject, wherein said quantity of ProC2 and the joint space width are predictive about the subject's risk for having good sensitivity or intermediate sensitivity to a treatment with said FGF-18 compound,
   b) selecting the subject having:
      good sensitivity to treatment with an FGF-18 compound as determined by the presence of (i) lower than 4.2±2SD ng/mL of ProC2, and (ii) JSW lower than or equal to 3.5±2SD mm,
      intermediate sensitivity to treatment with an FGF-18 compound as determined by the presence of (i) lower than 4.2±2SD ng/mL of ProC2, and (ii) JSW higher than 3.5±2SD mm, or
      intermediate sensitivity to treatment with an FGF-18 compound as determined by the presence of (i) higher than 4.2±2SD ng/ml of ProC2, and (ii) JSW lower than 3.5±2SD mm, and
   c) administering intraarticularly said FGF-18 compound to said selected subject,
   wherein the FGF-18 compound comprises amino acid residues 28-196 of SEQ ID NO: 1, optionally fused to a heterologous protein or chemical compound.

2. The method according to claim 1, wherein the cartilage disorder is selected from the group consisting of osteoarthritis, cartilage injury, fractures affecting joint cartilage, and surgical procedures with impact on joint cartilage.

3. A method for treating a subject with an FGF-18 compound having a cartilage disorder characterized by articular cartilage injury or loss of articular cartilage, comprising the following steps:
   a) determining, from a sample from said subject, the quantity of neo-epitope of Collagen type II (ProC2), and the measurement of the joint space width (JSW) in at least one knee of said subject, wherein said quantity of ProC2 and the joint space width are predictive about the subject's risk for intermediate sensitivity to a treatment with said FGF-18 compound,
   b) selecting the subject having:
      i) (a) lower than 4.2±2SD ng/ml of ProC2, and (b) JSW higher than 3.5±2SD mm, or
      ii) (a) higher than 4.2±2SD ng/mL of ProC2, and (b) JSW lower than 3.5±2SD mm, and
   c) administering intraarticularly said FGF-18 compound to said selected subject according to an alternative dosing regimen according to which the dose of the FGF-18 compound is increased, and/or the FGF-18 compound is administered for a longer treatment period compared to the usual dosing regimen for said FGF-18 compound,
   wherein the FGF-18 compound comprises amino acid residues 28-196 of SEQ ID NO: 1, optionally fused to a heterologous protein or chemical compound.

4. The method according to claim 3, wherein the cartilage disorder is selected from the group consisting of osteoarthritis, cartilage injury, fractures affecting joint cartilage, and surgical procedures with impact on joint cartilage.

5. The method of claim 1, wherein the FGF-18 compound is to be administered in a treatment cycle of once weekly for 3 weeks.

6. The method of claim 5, wherein the treatment cycle is repeated.

7. The method of claim 1, wherein the amount of FGF-18 compound is about 30-100 μg per administration.

8. The method of claim 7, wherein the amount of FGF-18 compound is about 30 μg per administration.

9. The method of claim 7, wherein the amount of FGF-18 compound is about 100 μg per administration.

10. The method of claim 1, wherein the FGF-18 compound is sprifermin or sprifermin fused to a heterologous protein or chemical compound.

11. The method of claim 3, wherein the FGF-18 compound is to be administered in a treatment cycle of once weekly for 3 weeks.

12. The method of claim 11, wherein the treatment cycle is repeated.

13. The method of claim 3, wherein the amount of FGF-18 compound is about 30-100 μg per administration.

14. The method of claim 13, wherein the amount of FGF-18 compound is about 100 μg per administration.

15. The method of claim 3, wherein the FGF-18 compound is sprifermin or sprifermin fused to a heterologous protein or chemical compound.

* * * * *

UNITED STATES PATENT AND TRADEMARK OFFICE
CERTIFICATE OF CORRECTION

PATENT NO. : 12,383,603 B2
APPLICATION NO. : 17/274457
DATED : August 12, 2025
INVENTOR(S) : Christoph H. Ladel et al.

Page 1 of 1

It is certified that error appears in the above-identified patent and that said Letters Patent is hereby corrected as shown below:

In the Specification

At Column 5, Line number 27, please delete "FGF-18 may be native (SEQ ID NO: 1)" and insert --"FGF-18 may be native (SEQ ID NO: 3)"--

At Column 5, Lines number 29 to 30, please delete "SEQ ID NO: 1" and insert --(SEQ ID NO: 3)"--

At Column 5, Line number 31, please delete "as shown in SEQ ID NO:2" and insert --"as shown in SEQ ID NO:4"--

At Column 5, Line number 32, please delete "2 to 170 of SEQ ID NO:2" and insert --"2 to 170 of SEQ ID NO:4"--

At Column 5, Line number 33, please delete "residues 28 to 196 of SEQ ID NO:1" and insert --"residues 28 to 196 of SEQ ID NO:3"--

In the Claims

Column 43, Line 40, In Claim 1, Line 20, delete "SEQ ID NO: 1" and insert --"SEQ ID NO:3"--

Column 44, Line 24, In Claim 3, Line 17, delete "SEQ ID NO: 1" and insert --"SEQ ID NO:3"--

Signed and Sealed this
Tenth Day of February, 2026

John A. Squires
*Director of the United States Patent and Trademark Office*

SEQUENCE LISTING

```
<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: recombinant Marker CTX-II

<400> SEQUENCE: 1

Glu Lys Gly Pro Asp Pro
1               5

<210> SEQ ID NO 2
<211> LENGTH: 10
<212> TYPE: PRT
<213> ORGANISM: Artificial Sequence
<220> FEATURE:
<223> OTHER INFORMATION: recombinant Marker ProC2

<400> SEQUENCE: 2

Gln Asp Val Arg Gln Pro Gly Pro Lys Gly
1               5                   10

<210> SEQ ID NO 3
<211> LENGTH: 207
<212> TYPE: PRT
<213> ORGANISM: Homo sapiens
<220> FEATURE:
<223> OTHER INFORMATION: Native human FGF-18

<400> SEQUENCE: 3

Met Tyr Ser Ala Pro Ser Ala Cys Thr Cys Leu Cys Leu His Phe Leu
1               5                   10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
        35                  40                  45

Arg Lys Gln Leu Arg Leu Tyr Gln Leu Tyr Ser Arg Thr Ser Gly Lys
    50                  55                  60
```

His Ile Gln Val Leu Gly Arg Arg Ile Ser Ala Arg Gly Glu Asp Gly
65                  70                  75                  80

Asp Lys Tyr Ala Gln Leu Leu Val Glu Thr Asp Thr Phe Gly Ser Gln
                85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
        195                 200                 205

<210> SEQ ID NO 4
<211> LENGTH: 170
<212> TYPE: PRT
<213> ORGANISM: Artificial Sequence
<220> FEATURE:
<223> OTHER INFORMATION: recombinant truncated FGF-18 (sprifermin)

<400> SEQUENCE: 4

Met Glu Glu Asn Val Asp Phe Arg Ile His Val Glu Asn Gln Thr Arg
1               5                   10                  15

Ala Arg Asp Asp Val Ser Arg Lys Gln Leu Arg Leu Tyr Gln Leu Tyr
            20                  25                  30

Ser Arg Thr Ser Gly Lys His Ile Gln Val Leu Gly Arg Arg Ile Ser
        35                  40                  45

Ala Arg Gly Glu Asp Gly Asp Lys Tyr Ala Gln Leu Leu Val Glu Thr
50                  55                  60

Asp Thr Phe Gly Ser Gln Val Arg Ile Lys Gly Lys Glu Thr Glu Phe
65                  70                  75                  80

Tyr Leu Cys Met Asn Arg Lys Gly Lys Leu Val Gly Lys Pro Asp Gly
                85                  90                  95

Thr Ser Lys Glu Cys Val Phe Ile Glu Lys Val Leu Glu Asn Asn Tyr
            100                 105                 110

Thr Ala Leu Met Ser Ala Lys Tyr Ser Gly Trp Tyr Val Gly Phe Thr
        115                 120                 125

Lys Lys Gly Arg Pro Arg Lys Gly Pro Lys Thr Arg Glu Asn Gln Gln
    130                 135                 140

Asp Val His Phe Met Lys Arg Tyr Pro Lys Gly Gln Pro Glu Leu Gln
145                 150                 155                 160

Lys Pro Phe Lys Tyr Thr Thr Val Thr Lys
                165                 170

<210> SEQ ID NO 5
<211> LENGTH: 32
<212> TYPE: PRT
<213> ORGANISM: Artificial Sequence
<220> FEATURE:
<223> OTHER INFORMATION: salmon calcitonin

<400> SEQUENCE: 5

```
Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30
```

<210> SEQ ID NO 6
<211> LENGTH: 396
<212> TYPE: PRT
<213> ORGANISM: Homo Sapiens
<220> FEATURE:
<223> OTHER INFORMATION: human BMP-2

<400> SEQUENCE: 6

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
```

-continued

```
                325                 330                 335
Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
            370                 375                 380

Tyr Gln Asp Met Val Val Glu Gly Cys Gly Cys Arg
385                 390                 395

<210> SEQ ID NO 7
<211> LENGTH: 431
<212> TYPE: PRT
<213> ORGANISM: Homo Sapiens
<220> FEATURE:
<223> OTHER INFORMATION: human BMP-7

<400> SEQUENCE: 7

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
```

```
                290                 295                 300
Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
            370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

<210> SEQ ID NO 8
<211> LENGTH: 501
<212> TYPE: PRT
<213> ORGANISM: Homo Sapiens
<220> FEATURE:
<223> OTHER INFORMATION: human GDF-5

<400> SEQUENCE: 8

```
Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
                20                  25                  30

Gln Arg Pro Gln Gly Thr Arg Pro Gly Leu Ala Lys Ala Glu Ala Lys
            35                  40                  45

Glu Arg Pro Pro Leu Ala Arg Asn Val Phe Arg Pro Gly Gly His Ser
50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
                100                 105                 110

Gln Thr Arg Gln Ala Thr Ala Arg Thr Val Thr Pro Lys Gly Gln Leu
            115                 120                 125

Pro Gly Gly Lys Ala Pro Pro Lys Ala Gly Ser Val Pro Ser Ser Phe
130                 135                 140

Leu Leu Lys Lys Ala Arg Glu Pro Gly Pro Pro Arg Glu Pro Lys Glu
145                 150                 155                 160

Pro Phe Arg Pro Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
            180                 185                 190

Lys Leu Glu Ala Gly Leu Ala Asn Thr Ile Thr Ser Phe Ile Asp Lys
            195                 200                 205

Gly Gln Asp Asp Arg Gly Pro Val Val Arg Lys Gln Arg Tyr Val Phe
210                 215                 220

Asp Ile Ser Ala Leu Glu Lys Asp Gly Leu Leu Gly Ala Glu Leu Arg
```

```
                    225                 230                 235                 240
Ile Leu Arg Lys Lys Pro Ser Asp Thr Ala Lys Pro Ala Ala Pro Gly
                245                 250                 255

Gly Gly Arg Ala Ala Gln Leu Lys Leu Ser Ser Cys Pro Ser Gly Arg
            260                 265                 270

Gln Pro Ala Ser Leu Leu Asp Val Arg Ser Val Pro Gly Leu Asp Gly
            275                 280                 285

Ser Gly Trp Glu Val Phe Asp Ile Trp Lys Leu Phe Arg Asn Phe Lys
        290                 295                 300

Asn Ser Ala Gln Leu Cys Leu Glu Leu Glu Ala Trp Glu Arg Gly Arg
305                 310                 315                 320

Ala Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
            340                 345                 350

Leu Phe Phe Asn Glu Ile Lys Ala Arg Ser Gly Gln Asp Asp Lys Thr
        355                 360                 365

Val Tyr Glu Tyr Leu Phe Ser Gln Arg Arg Lys Arg Arg Ala Pro Leu
370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
            420                 425                 430

Cys Glu Phe Pro Leu Arg Ser His Leu Glu Pro Thr Asn His Ala Val
        435                 440                 445

Ile Gln Thr Leu Met Asn Ser Met Asp Pro Glu Ser Thr Pro Pro Thr
        450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
                485                 490                 495

Ser Cys Gly Cys Arg
            500

<210> SEQ ID NO 9
<211> LENGTH: 288
<212> TYPE: PRT
<213> ORGANISM: Homo Sapiens
<220> FEATURE:
<223> OTHER INFORMATION: human FGF-beta

<400> SEQUENCE: 9

Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
```

```
                    85                  90                  95
Gly Arg Gly Arg Ala Pro Glu Arg Val Gly Arg Gly Arg Gly Arg
                100                 105                 110
Gly Thr Ala Ala Pro Arg Ala Ala Pro Ala Ala Arg Gly Ser Arg Pro
                115                 120                 125
Gly Pro Ala Gly Thr Met Ala Ala Gly Ser Ile Thr Thr Leu Pro Ala
                130                 135                 140
Leu Pro Glu Asp Gly Gly Ser Gly Ala Phe Pro Pro Gly His Phe Lys
145                 150                 155                 160
Asp Pro Lys Arg Leu Tyr Cys Lys Asn Gly Gly Phe Phe Leu Arg Ile
                165                 170                 175
His Pro Asp Gly Arg Val Asp Gly Val Arg Glu Lys Ser Asp Pro His
                180                 185                 190
Ile Lys Leu Gln Leu Gln Ala Glu Glu Arg Gly Val Val Ser Ile Lys
                195                 200                 205
Gly Val Cys Ala Asn Arg Tyr Leu Ala Met Lys Glu Asp Gly Arg Leu
                210                 215                 220
Leu Ala Ser Lys Cys Val Thr Asp Glu Cys Phe Phe Phe Glu Arg Leu
225                 230                 235                 240
Glu Ser Asn Asn Tyr Asn Thr Tyr Arg Ser Arg Lys Tyr Thr Ser Trp
                245                 250                 255
Tyr Val Ala Leu Lys Arg Thr Gly Gln Tyr Lys Leu Gly Ser Lys Thr
                260                 265                 270
Gly Pro Gly Gln Lys Ala Ile Leu Phe Leu Pro Met Ser Ala Lys Ser
                275                 280                 285

<210> SEQ ID NO 10
<211> LENGTH: 208
<212> TYPE: PRT
<213> ORGANISM: Homo Sapiens
<220> FEATURE:
<223> OTHER INFORMATION: human FGF-9

<400> SEQUENCE: 10

Met Ala Pro Leu Gly Glu Val Gly Asn Tyr Phe Gly Val Gln Asp Ala
1               5                   10                  15
Val Pro Phe Gly Asn Val Pro Val Leu Pro Val Asp Ser Pro Val Leu
                20                  25                  30
Leu Ser Asp His Leu Gly Gln Ser Glu Ala Gly Gly Leu Pro Arg Gly
                35                  40                  45
Pro Ala Val Thr Asp Leu Asp His Leu Lys Gly Ile Leu Arg Arg Arg
50                  55                  60
Gln Leu Tyr Cys Arg Thr Gly Phe His Leu Glu Ile Phe Pro Asn Gly
65                  70                  75                  80
Thr Ile Gln Gly Thr Arg Lys Asp His Ser Arg Phe Gly Ile Leu Glu
                85                  90                  95
Phe Ile Ser Ile Ala Val Gly Leu Val Ser Ile Arg Gly Val Asp Ser
                100                 105                 110
Gly Leu Tyr Leu Gly Met Asn Glu Lys Gly Glu Leu Tyr Gly Ser Glu
                115                 120                 125
Lys Leu Thr Gln Glu Cys Val Phe Arg Glu Gln Phe Glu Glu Asn Trp
                130                 135                 140
Tyr Asn Thr Tyr Ser Ser Asn Leu Tyr Lys His Val Asp Thr Gly Arg
145                 150                 155                 160
Arg Tyr Tyr Val Ala Leu Asn Lys Asp Gly Thr Pro Arg Glu Gly Thr
```

```
              165                 170                 175
Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
            195                 200                 205
```